United States Patent
Pudil et al.

(10) Patent No.: US 10,478,545 B2
(45) Date of Patent: Nov. 19, 2019

(54) PARALLEL MODULES FOR IN-LINE RECHARGING OF SORBENTS USING ALTERNATE DUTY CYCLES

(71) Applicant: Medtronic, Inc., Minneapolis, MN (US)

(72) Inventors: Bryant J. Pudil, Plymouth, MN (US); Martin T. Gerber, Maple Grove, MN (US); David B. Lura, Maple Grove, MN (US); Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 15/869,296

(22) Filed: Jan. 12, 2018

(65) Prior Publication Data

US 2018/0133387 A1    May 17, 2018

Related U.S. Application Data

(63) Continuation of application No. 14/259,589, filed on Apr. 23, 2014, now Pat. No. 9,884,145.

(Continued)

(51) Int. Cl.
| | |
|---|---|
| *A61M 1/16* | (2006.01) |
| *B01D 15/18* | (2006.01) |
| *B01D 15/22* | (2006.01) |
| *B01J 39/12* | (2006.01) |
| *B01J 20/06* | (2006.01) |

(Continued)

(52) U.S. Cl.
CPC ....... *A61M 1/1696* (2013.01); *B01D 15/1871* (2013.01); *B01D 15/22* (2013.01); *B01J 20/0211* (2013.01); *B01J 20/0292* (2013.01); *B01J 20/06* (2013.01); *B01J 20/08* (2013.01); *B01J 20/20* (2013.01);
(Continued)

(58) Field of Classification Search
None
See application file for complete search history.

(56) References Cited

U.S. PATENT DOCUMENTS

| | | | |
|---|---|---|---|
| 1,617,288 A | 2/1927 | Kenney | |
| 2,703,313 A | 1/1950 | Gill | |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.

(Continued)

*Primary Examiner* — Richard C Gurtowski
(74) *Attorney, Agent, or Firm* — Kenneth Collier; Roger Hahn

(57) ABSTRACT

Parallel modules for in-line recharging of sorbent materials using alternate duty cycles for a sorbent cartridge. The sorbent cartridge can have two or more modules contained therein having connectors connecting each of the modules. One or more of the modules can be reusable and the sorbent materials therein can be recharged.

12 Claims, 22 Drawing Sheets

Related U.S. Application Data

(60) Provisional application No. 61/945,073, filed on Feb. 26, 2014, provisional application No. 61/941,672, filed on Feb. 19, 2014, provisional application No. 61/909,372, filed on Nov. 26, 2013.

(51) Int. Cl.

| | | |
|---|---|---|
| *B01J 20/08* | (2006.01) | |
| *B01J 20/20* | (2006.01) | |
| *B01J 20/02* | (2006.01) | |
| *B01J 20/28* | (2006.01) | |
| *G01N 30/60* | (2006.01) | |

(52) U.S. Cl.
CPC ......... *B01J 20/28052* (2013.01); *B01J 39/12* (2013.01); *B01J 2220/62* (2013.01); *G01N 30/6091* (2013.01)

(56) References Cited

U.S. PATENT DOCUMENTS

| | | |
|---|---|---|
| 3,608,729 A | 9/1971 | Haselden |
| 3,617,545 A | 11/1971 | Dubois |
| 3,617,558 A | 11/1971 | Jones |
| 3,669,878 A | 6/1972 | Marantz |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Colman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |

(56) References Cited

U.S. PATENT DOCUMENTS

| | | |
|---|---|---|
| 7,597,806 B2 | 10/2009 | Uchi |
| 7,674,231 B2 | 3/2010 | McCombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0131332 A1 | 6/2005 | Kelly |
| 2005/0126998 A1 | 7/2005 | Childers |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0217771 A1 | 2/2006 | Soykan |
| 2006/0157413 A1 | 7/2006 | Bene |
| 2006/0189926 A1 | 8/2006 | Hall et al. |
| 2006/0195064 A1 | 8/2006 | Plahey |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |

(56) References Cited

U.S. PATENT DOCUMENTS

| | | |
|---|---|---|
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114001 A1 | 5/2010 | O'Mahony |
| 2010/0114012 A1 | 5/2010 | Sandford |
| 2010/0137693 A1 | 6/2010 | Porras |
| 2010/0168546 A1 | 7/2010 | Kamath |
| 2010/0168641 A1 | 7/2010 | O'Mahony et al. |
| 2010/0213127 A1 | 8/2010 | Castellarnau |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2013/0333795 A1* | 12/2013 | Balschat ............... A61M 1/14 141/1 |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

(56) References Cited

U.S. PATENT DOCUMENTS

| | | | |
|---|---|---|---|
| 2016/0243540 A1 | 8/2016 | Menon | |
| 2016/0243541 A1 | 8/2016 | Menon | |

FOREIGN PATENT DOCUMENTS

| | | | |
|---|---|---|---|
| CN | 103402563 A | 11/2013 | |
| CN | 104936633 | 9/2015 | |
| CN | 105658326 A | 6/2016 | |
| DE | 3110128 A1 | 9/1982 | |
| DE | 102011052188 | 1/2013 | |
| EP | 266795 A2 | 11/1987 | |
| EP | 0264695 | 4/1988 | |
| EP | 0614081 A1 | 10/1993 | |
| EP | 0614081 B1 | 7/2000 | |
| EP | 711182 B1 | 6/2003 | |
| EP | 1364666 A1 | 11/2003 | |
| EP | 0906768 B1 | 2/2004 | |
| EP | 1701752 A2 | 9/2006 | |
| EP | 1450879 | 10/2008 | |
| EP | 1991289 | 11/2008 | |
| EP | 1592494 B1 | 6/2009 | |
| EP | 2100553 A1 | 9/2009 | |
| EP | 2575827 A2 | 12/2010 | |
| EP | 2576453 A2 | 12/2011 | |
| EP | 2446908 | 5/2012 | |
| EP | 2701580 | 11/2012 | |
| EP | 2701595 | 11/2012 | |
| EP | 1545652 B1 | 1/2013 | |
| EP | 1684625 B1 | 1/2013 | |
| EP | 2142234 B1 | 1/2013 | |
| EP | 2550984 A1 | 1/2013 | |
| EP | 1345856 B1 | 3/2013 | |
| EP | 1938849 B1 | 3/2013 | |
| EP | 2219703 B1 | 3/2013 | |
| EP | 2564884 A1 | 3/2013 | |
| EP | 2564885 A1 | 3/2013 | |
| EP | 2344220 B1 | 4/2013 | |
| EP | 1345687 | 6/2013 | |
| EP | 2701596 | 3/2014 | |
| JP | S5070281 A | 6/1975 | |
| JP | S51-55193 | 5/1976 | |
| JP | S51-131393 | 11/1976 | |
| JP | S61164562 | 7/1986 | |
| JP | 2981573 | 11/1999 | |
| JP | 2005511250 | 4/2005 | |
| JP | H4-90963 | 5/2005 | |
| JP | 2007-44602 A | 2/2007 | |
| JP | 200744602 | 2/2007 | |
| JP | 200744602 A | 2/2007 | |
| JP | 5099464 | 10/2012 | |
| JP | 2013502987 | 10/2013 | |
| WO | 9106326 A1 | 5/1991 | |
| WO | 9532010 A1 | 11/1995 | |
| WO | 9937342 | 7/1999 | |
| WO | 2000038591 A2 | 7/2000 | |
| WO | 0057935 | 10/2000 | |
| WO | 200066197 A1 | 11/2000 | |
| WO | 200170307 A1 | 9/2001 | |
| WO | 2001085295 A2 | 9/2001 | |
| WO | 0185295 A2 | 11/2001 | |
| WO | 2002043859 | 6/2002 | |
| WO | 2003043677 A2 | 5/2003 | |
| WO | 2003043680 | 5/2003 | |
| WO | WO 2003041764 | 5/2003 | |
| WO | 2003051422 A2 | 6/2003 | |
| WO | 2004008826 | 1/2004 | |
| WO | 2004009156 | 1/2004 | |
| WO | 2004030716 A2 | 4/2004 | |
| WO | 2004030717 A2 | 4/2004 | |
| WO | 2004064616 A2 | 8/2004 | |
| WO | 2004062710 A3 | 10/2004 | |
| WO | WO 2005/062973 A3 | 7/2005 | |
| WO | 2005123230 | 12/2005 | |
| WO | 2005123230 A2 | 12/2005 | |
| WO | 2007089855 A2 | 8/2007 | |
| WO | WO 20070103411 | 9/2007 | |
| WO | 2008075951 A1 | 6/2008 | |
| WO | 2009026603 | 12/2008 | |
| WO | 2009026603 A1 | 3/2009 | |
| WO | 2009064984 | 5/2009 | |
| WO | 2009157877 A1 | 12/2009 | |
| WO | 2009157878 A1 | 12/2009 | |
| WO | 20090157877 | 12/2009 | |
| WO | 2010028860 | 3/2010 | |
| WO | 2010028860 A1 | 3/2010 | |
| WO | 2010102190 A4 | 11/2010 | |
| WO | 2010141949 | 12/2010 | |
| WO | WO 2011/017215 | 2/2011 | |
| WO | 2011025705 A1 | 3/2011 | |
| WO | 2012148781 | 11/2012 | |
| WO | 2012148786 | 11/2012 | |
| WO | 2012148789 | 11/2012 | |
| WO | 2012162515 A2 | 11/2012 | |
| WO | 20120277551 | 11/2012 | |
| WO | 2012172398 | 12/2012 | |
| WO | 2013019179 | 2/2013 | |
| WO | 2013019179 A1 | 2/2013 | |
| WO | 2013019994 A2 | 2/2013 | |
| WO | 2013022024 A1 | 2/2013 | |
| WO | 2013022837 A1 | 2/2013 | |
| WO | 2013025844 | 2/2013 | |
| WO | 2013025957 | 2/2013 | |
| WO | 2013027214 | 2/2013 | |
| WO | 2013028809 | 2/2013 | |
| WO | 2013028809 A3 | 2/2013 | |
| WO | WO 2013/019179 | 2/2013 | |
| WO | WO 2013/019994 | 2/2013 | |
| WO | WO 2013-025957 | 2/2013 | |
| WO | WO 2013-028809 | 2/2013 | |
| WO | WO 2013/028809 | 2/2013 | |
| WO | WO 2013019179 | 2/2013 | |
| WO | 2013030642 A1 | 3/2013 | |
| WO | 2013030643 A1 | 3/2013 | |
| WO | 2013019994 A3 | 4/2013 | |
| WO | 2012060700 | 5/2013 | |
| WO | 2012162515 A3 | 5/2013 | |
| WO | 2013025844 A3 | 5/2013 | |
| WO | 2013101888 | 7/2013 | |
| WO | 2013103607 A1 | 7/2013 | |
| WO | 2013103906 | 7/2013 | |
| WO | WO 2013/103607 | 7/2013 | |
| WO | WO 2013109922 | 7/2013 | |
| WO | 2013114063 A1 | 8/2013 | |
| WO | 2013121162 A1 | 8/2013 | |
| WO | 14066254 | 5/2014 | |
| WO | 14066255 | 5/2014 | |
| WO | 14077082 | 5/2014 | |
| WO | 2014121162 | 8/2014 | |
| WO | 2014121163 | 8/2014 | |
| WO | 2014121167 | 8/2014 | |
| WO | 2014121169 | 8/2014 | |
| WO | 2015060914 | 4/2015 | |
| WO | WO 2015/080895 | 4/2015 | |
| WO | WO 2015060914 | 4/2015 | |
| WO | WO 2015/126879 | 8/2015 | |
| WO | 2015142624 | 9/2015 | |
| WO | 2015199764 | 12/2015 | |
| WO | 2015199765 | 12/2015 | |
| WO | 2015199863 | 12/2015 | |
| WO | 2015199864 | 12/2015 | |
| WO | WO 2015-199863 | 12/2015 | |
| WO | WO 2015-199864 | 12/2015 | |
| WO | WO 2015199765 | 12/2015 | |
| WO | WO 2016/191039 | 12/2016 | |

OTHER PUBLICATIONS

European Search Report for App. No. 15812081.6, dated Mar. 8, 2018.

European Search Report for EP App. No. 15811326.6, dated Feb. 14, 2018.

European Search Report for EP App. No. 15812413.1, dated Feb. 2, 2018.

(56) References Cited

OTHER PUBLICATIONS

U.S. Appl. No. 13/100,847, filed Nov. 10, 2011, C-Tech BioMedical Inc.
U.S. Appl. No. 13/565,733, filed Aug. 2, 2012, Medtronic.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
U.S. Appl. No. 61/760,033, filed Feb. 1, 2013, Medtronic.
U.S. Appl. No. 14/637,606_OA.
U.S. Appl. No. 14/645,394_OA.
[NPL105] Brynda, Et. Al., The detection of toman 2-microglcbuiin by grating coupler immunosensor with three dimensional antibody networks. Biosensors & Bioelectronics, 1999, 363-368, 14(4).
[NPL111] Zhong, Et. Al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL138] U.S. Appl. No. 61/480,544.
[NPL139] U.S. Appl. No. 61/480,541, filed Apr. 29, 2011.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, dated Jul. 6, 2012.
[NPL147] PCT/US2012/034335, International Search Report, dated Sep. 5, 2012.
[NPL148] PCT/US/2012/034327, International Search Report, dated Aug. 13, 2013.
[NPL149] PCT/US/2012/034329, International Search Report, dated Dec. 3, 2012.
[NPL162] International Search Report from PCT/US2012/051946 dated Mar. 4, 2013.
[NPL163] U.S. Appl. No. 61/526,209.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion dated Mar. 9, 2015.
[NPL176] Bleyer, Et. Al., Sudden and cardiac death rated in hemodialysis patients, Kidney International. 1999, 1553-1559: 55.
[NPL187] PCT/US2012/034333, International Preliminary Report on Patentability, dated Oct. 29, 2013.
[NPL188] PCT/US2012/034333, International Search Report, dated Aug. 29, 2012.
[NPL188] PCT/US2012/034333, International Search Report, dated Aug. 29, 2013.
[NPL197] PCT/US2012/034330, International Preliminary Report on Patentability, dated Oct. 29, 2013.
[NPL1] PCT/US2014/065950 International Search Report and Written Opinion dated Feb. 24, 2015.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL217] U.S. Appl. No. 13/757,722, filed Feb. 1, 2013.
[NPL218] U.S. Appl. No. 13/757,794, filed Feb. 2, 2012.
[NPL219] U.S. Appl. No. 13/791,755, filed Mar. 8, 2013.
[NPL21] U.S. Appl. No. 13/424,479, filed Nov. 1, 2012.
[NPL220] U.S. Appl. No. 13/757,792, filed Feb. 2, 2013.
[NPL222] U.S. Appl. No. 13/757,794, filed Feb. 2, 2013.
[NPL227] U.S. Appl. No. 13/837,287, filed Mar. 15, 2013.
[NPL22] U.S. Appl. No. 13/424,429, filed Nov. 1, 2012.
[NPL230] Redfield, Et. Al, Restoration of renal response to atria! natriuretic factor in experimental low-output heat failure, Am. J. Physiol., Oct. 1, 1989, R917-923:257.
[NPL231] Rogoza, Et. Al., Validation of A&D UA-767 device for the self-measurement of blood pressure, Blood Pressure Monitoring, 2000, 227-231, 5(4).
[NPL234] Lima, Et. Al., An electrochemical sensor based on nanostructure hollsndite-type manganese oxide for detection of potassium ion, Sensors, Aug. 24, 2009, 6613-8625, 9.
[NPL235] Maclean, Et, Al., Effects of hindlimb contraction on pressor and muscle interstitial metabolite responses in the cat, J. App. Physiol., 1998, 1583-1592, 85(4).
[NPL237] U.S. Appl. No. 13/757,693, filed Feb. 1, 2013.
[NPL238] PCT Application, PCT/US20013/020404, filed Jan. 4, 2013.
[NPL23] U.S. Appl. No. 13/424,525.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL246] PCT/US2014/014346 International Search Report and Written Opinion.
[NPL247] U.S. Appl. No. 13/835,735, filed Mar. 15, 2013.
[NPL248] PCT/US2014/014345 International Search Report and Written Opinion, dated May 2014.
[NPL250] U.S. Appl. No. 13/835,735 IDS, filed Jun. 13, 2013.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, Et. Al., Activity-induced recovery of excitability in K+-depressed rat soleus muscle, Am. J. P 280: R48-R55, Jan. 1, 2001.
[NPL27] Overgaard. Et. Al., Relations between excitability and contractility in rate soleusmuscle: role of the NA+-K+ pump and NA+-K—S gradients. Journal of Physiology, 1999, 215-225, 518(1).
[NPL2] PCT/US2015/032492 International Search Report dated Nov. 19, 2015.
[NPL306] Coast, Et Al. 1990, An approach to Cardiac Arrhythmia analysis Using Hidden Markov Models, IEEE Transactions on Biomedical Engineering. 1990, 37(9):826-835.
[NPL310] U.S. Appl. No. 61/480,532.
[NPL317] U.S. Appl. No. 61/480,530.
[NPL318] U.S. Appl. No. 61/480,528, filed Apr. 29, 2011.
[NPL32] Secemsky, Et. Al, High prevalence of cardiac autonomic dysfunction and T-wave alternans in dialysis patients. Heart Rhythm, Apr. 2011, 592-598 : vol. 8, No. 4.
[NPL35] Wei, Et. Al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL37] U.S. Appl. No. 13/368,225, filed Feb. 7, 2012.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column, World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL387] Gotch FA, Sargent JA A mechanistic analysis of the National Cooperative Dialysis Study (NCDS). Kidney int. 1985: 28:526-34.
[NPL388] Daugirdas JT. Second generation logarithmic estimates of single-pool variable volume Kt/V and analysis of error. J Am Soc Nephrol, 1993: 4:1205-13.

(56) References Cited

OTHER PUBLICATIONS

[NPL389] Steil et al. Intl Journ Artif Organs, 1993, In Vivo Verification of an Automatic Noninvasive System for Real Time Kt Evaluation, Asaio J., 1993, 39:M348-52.
[NPL39] PCT/US2012/034332, International Search Report, dated Jul. 5, 2012.
[NPL3] PCT/US2015/019901 International Search Report and Written Opinion dated Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL47] U.S. Appl. No. 61/480,544.
[NPL494] John Wm Agar: Review: Understanding sorbent dialysis systems, Nephrology, vol. 15, No. 4, Jun. 1, 2010, pp. 406-411.
[NPL499] EP. App. 14746193.3 Search Report dated Oct. 19, 2016.
[NPL4] PCT/US2015/016270 International Search Report and Written Opinion dated Jun. 5, 2015.
[NPL518] Office Action in U.S. Appl. No. 14/269,589, dated Nov. 4, 2016.
[NPL519] Office Action in U.S. Appl. No. 13/586,824 dated Dec. 21, 2015.
[NPL520] Office Action in U.S. Appl. No. 13/586,824 dated Jun. 4, 2015.
[NPL532] Eureopean Search Report for App. No. EP14745643 dated Oct. 6, 2016.
[NPL534] Office Action in U.S. Appl. No. 13/586,824 dated Dec. 21, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 Asaio J. 372, 372-375 (2005).
[NPL554] St. Peter et al., Liver and kidney preservation by perfusion, 359 the Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 dated Jan. 11, 2016.
[NPL559] Office Action in U.S. Appl. No. 13/565,733 dated Jun. 11, 2015.
[NPL55] U.S. Appl. No. 13/424,454.
[NPL560] Office Action in U.S. Appl. No. 13/586,824 dated Jun. 4, 2015.
[NPL561] Office Action in U.S. Appl. No. 13/757,792 dated Jun. 2, 2016.
[NPL562] Office Action in U.S. Appl. No. 13/757,796 dated Apr. 13, 2015.
[NPL563] Office Action in U.S. Appl. No. 13/757,796 dated Dec. 21, 2015.
[NPL564] Office Action in U.S. Appl. No. 13/835,735 dated Oct. 13, 2015.
[NPL565] Office Action in U.S. Appl. No. 13/836,079 dated Apr. 17, 2015.
[NPL566] Office Action in U.S. Appl. No. 13/836,079 dated Jun. 30, 2016.
[NPL569] Office Action in U.S. Appl. No. 13/791,755 dated Mar. 16, 2016.
[NPL570] Office Action in U.S. Appl. No. 13/791,755 dated Aug. 9, 2016.
[NPL571] Office Action in U.S. Appl. No. 13/835,735 dated Jun. 16, 2016.
[NPL572] Office Action in U.S. Appl. No. 13/836,079 dated Nov. 6, 2015.
[NPL57] U.S. Appl. No. 13/424,467.
[NPL584] Office Action in App. No. AU 2015280604 dated Apr. 8, 2016.
[NPL586] International Search Report from International Application No. PCT/US2014/014347 dated May 9, 2014.
[NPL590] PCT/US2016/030319 Written Opinion dated Jul. 27, 2016.
[NPL591] PCT/US2016/030320 Written Opinion dated Jul. 27, 2016.
[NPL596] PCT/US2012/014347, International Search Report.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.
[NPL623] PCT/US2015/032485 Written Opinion dated Oct. 16, 2016.
[NPL626] PCT/US2015/032485 International Search Report and Written Opinion dated Oct. 16, 2015.
[NPL62] U.S. Appl. No. 13/424,533.
[NPL634] PCT/US2016/030320 International Preliminary Report on Patentability, dated Apr. 20, 2017.
[NPL654] International Preliminary Report from International Application No. PCT/US2014/014348 dated Jan. 9, 2015.

(56) References Cited

OTHER PUBLICATIONS

[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL670] Office Action in European Application No. 14746415.0 dated Apr. 19, 2017.
[NPL67] U.S. Appl. No. 13/424,490.
[NPL681] PCT/US2015/020047 International Search Report and Written Opinion dated Jun. 29, 2015.
[NPL682] PCT/US2015/020047 International Preliminary Report on Patentability dated Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL68] U.S. Appl. No. 13/424,517.
[NPL690] US2015/019881 International Search Report and Written Opinion dated Jun. 29, 2015.
[NPL692] PCT/US2014/065950 International Preliminary Report on Patentability dated Oct. 28, 2015.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL736] Office Action in European Application No. 14746193.3 dated Apr. 19, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL81] U.S. Appl. No. 61/480,539, filed Apr. 29, 2011.
[NPL84] U.S. Appl. No. 61/480,535, filed Apr. 29, 2011.
[NPL8] PCT/US2015/020044 International Search Report Written Opinion dated Jun. 30, 2015.
[NPL90] Nedelkov, Et. Al., Design of buffer exchange surfaces and sensor chips for biosensor chip mass spectrometry, Proteomics, 2002, 441-446, 2(4).
[NPL] European Search Report App 14865374.4, dated Jun. 12, 2017.
Chinese Office Action in App. No. 201580009563.X, dated Mar. 13, 2018.
European Search Report for App. No. 18153940.4, dated Jun. 12, 2018.
European Search Report for EP 15811439, dated Feb. 15, 2018.
European Search Report for EP App. No. 15810804.3, dated Feb. 15, 2018.
European Search Report for EP App. No. 15811573.3, dated Feb. 15, 2018.
European Search Report in EP 15811454, dated Feb. 15, 2018.
European Search Report in EP 15812559.1, dated Jan. 31, 2018.
PCT/US2016/030304_IPRP.
PCT/US2016/030319_IPRP.
Search Report for EP App. No. 17203984.4, dated Mar. 29, 2018.
Search Report in EP App. No. 15752771, dated Nov. 22, 2017.
Office Action in Japanese Application No. 2016-553344, dated Apr. 24, 2018.

* cited by examiner

PARALLEL MODULES FOR IN-LINE RECHARGING OF SORBENTS USING ALTERNATE DUTY CYCLES

CROSS-REFERENCE TO RELATED APPLICATION

This application is a continuation of U.S. patent application Ser. No. 14/259,589 filed Apr. 23, 2014, which claims the benefit of and priority to U.S. Provisional Patent Application No. 61/945,073 filed Feb. 26, 2014, U.S. Provisional Patent Application No. 61/941,672 filed Feb. 19, 2014, U.S. Provisional Patent Application No. 61/909,372 filed Nov. 26, 2013, the entire disclosure of which is incorporated by reference herein.

FIELD OF THE INVENTION

The invention relates to parallel modules for in-line recharging sorbents using alternate duty cycles for a sorbent cartridge.

BACKGROUND

Dialysis involves the movement of blood through a dialyzer that has a semi-permeable membrane. Simultaneously, dialysate is circulated through the dialyzer on an opposite side of the semi-permeable membrane. Toxins present in the blood stream of the patient pass from the blood through the membrane into the dialysate. After passing through the dialyzer, the spent dialysate is discarded. Disposal of spent dialysate requires a large amount of source water for preparing the replacement dialysate necessary for use during continuous dialysis. However, in sorbent dialysis systems, the spent dialysate is re-circulated through a sorbent cartridge rather than being discarded. The sorbent cartridge contains layers of sorbent material which selectively remove specific toxins, or break down toxins, in the dialysate.

The advantage of sorbent dialysis is that a much lower amount of water is required. In four hours of traditional dialysis, up to 120 L of water may be required to generate the dialysate. By contrast, using sorbent dialysis, as little as 6 or 7 L of water may be necessary. Thus, the need for drains and a continuous source of purified water are eliminated, rendering the system portable.

One of the drawbacks of sorbent dialysis systems is the high cost. The materials used in the sorbent cartridges can be expensive. Disposing of the cartridges after each use generates waste and drives up costs. Other known dialysate fluid circulation systems and apparatuses have separate housings where a first housing has a material capable of releasing sodium into dialysate fluid flowing through the first housing, and a second housing has a material capable of binding sodium ions from dialysate fluid flowing through the second housing. However, such systems cannot be formed into a single housing design, oftentimes require many liters of water, and may not be portable. The systems also do not provide for recharging some or all of the components of a sorbent cartridge that would allow reuse of specific components and enable lower long-term costs for operating such systems.

Hence, there is a need for a sorbent cartridge having separation of materials within the sorbent cartridge into modules to allow for isolation of those materials. There is a need for a sorbent cartridge providing for isolation of one or more sorbent materials to allow for cheaper or non-reusable materials to be discarded, while more expensive and reusable materials are recharged. There is a further need for a unitary sorbent cartridge having multiple discreet modules that can be easily connected and/or detached from the unitary sorbent cartridge thereby facilitating the recharging and/or recycling of the sorbent materials and the sorbent cartridge while retaining a single unitary design. There is also a need for a sorbent cartridge having the features of reduced size and weight necessary for a portable dialysis machine. There is a need for a modular sorbent cartridge wherein the sorbent materials can be arranged within the modules of the cartridge to allow for isolation of particular materials or groups of materials. There is a further need for any one of the modules in the cartridge to be reusable or optionally detachable from the cartridge to allow any one of disposal, recycling or recharging of sorbent material within the module. There is a need for a sorbent cartridge having specific materials that can be recharged and allowing for disposal of less expensive materials.

There is a need for the sorbent materials to be recharged without removing the modules from the sorbent cartridge during operation, making the system easier to use. There is a need for a recharging means directly attached to the sorbent modules, to allow the modules to be recharged simply by directing fluid flow from the rechargers to the module. There is further a need for one or more of the modules to be removable to allow for the recycling and/or disposal of these modules, while allowing the recharging of other modules. There is a need for recharging the sorbent modules in an alternate duty cycle to recharge the material without disrupting the other modules.

SUMMARY OF THE INVENTION

The invention relates to a modular sorbent cartridge having modules positioned parallel to one another. The sorbent cartridges can be reusable or non-reusable.

In one embodiment, the sorbent cartridge can have at least two modules such that at least two modules are positioned parallel to one another. The modules can have one or more connectors fluidly connectable to any one of a fluid flow path, a wash line wherein the wash line is fluidly connectable to a recharger, and a bypass line wherein the bypass line is fluidly connectable to another module or fluid flow path.

In any embodiment, the modules can be configured to be in an offline state by being fluidly connectable to one or more recharger, and at least one of the modules can be configured to be in an online state by being fluidly connectable to any one of the fluid flow path or the bypass line.

In another embodiment, the modular sorbent cartridge can have valves positioned before and/or after the modules on the connectors to selectively direct flow through the modules, fluid flow paths, wash lines, or bypass lines. In another embodiment, the modular sorbent cartridge can have valves positioned before and/or after the modules on the connectors to selectively direct flow through the modules. In any embodiment, the valve can be any one or two-way, three-way, four-way valves or combinations thereof.

In one embodiment, a first module can be positioned in series before a second and third module, wherein the second and third module can be positioned parallel to one another. The first module can be connected to a first connector; the first connector having a first valve, wherein the first valve can connect the first connector, a second connector, a third connector, and a fourth connector. The second connector can connect the first valve to the second module. The third connector can connect the first valve to the third module. The fourth connector can connect the first valve to a second valve, wherein the second valve can connect the fourth connector, a fifth connector, a sixth connector, and a seventh connector. The fifth connector can connect the second valve to the second module. The sixth connector can connect the second valve to the third module. The seventh connector can connect the second valve to another section of the sorbent cartridge.

In another embodiment, a first module can be positioned in series before a second and third module, wherein the second and third module can be positioned parallel to one another. The first module can be connected to a first connector; the first connector having a first valve, wherein the first valve can connect the first connector, a second connector, a third connector, and a fourth connector. The second connector can connect the first valve to a second valve, wherein the second valve can connect the second connector, a first wash line and the second module. The first wash line can connect the second valve to a first recharger connector. The third connector can connect the first valve to a third valve, wherein the third valve can connect the third connector, a second wash line and the third module. The second wash line can connect the third valve to a second recharger connector. The fourth connector can connect the first valve to a sixth valve, wherein the sixth valve can connect the fourth connector, a fifth connector, a sixth connector, and a seventh connector. The fifth connector can connect the sixth valve to a fourth valve, wherein the fourth valve can connect the fifth connector, a third wash line and the second module. The third wash line can connect the fourth valve to a third recharger connector. The sixth connector can connect the sixth valve to a fifth valve, wherein the fifth valve can connect the sixth connector, a fourth wash line and the third module. The fourth wash line can connect the fifth valve to a fourth recharger connector. The seventh connector can connect the sixth valve to another section of the sorbent cartridge.

In another embodiment, a first and second module can be positioned parallel to one another, a third and fourth module can be positioned parallel to one another, and the first and second modules can be in series with the third and fourth modules, respectively. A first valve can connect a first, second, third and fourth connector. The second connector can connect the first valve to a second valve. The second valve can connect the second connector, a first wash line and the first module. The first wash line can connect the second valve to a first recharger connector. The third connector can connect the first valve to a third valve. The third valve can connect the third connector, a second wash line, and the second module. The second wash line can connect the third valve to a second recharger connector. The fourth connector can connect the first valve to a tenth valve. The tenth valve can connect the fourth connector, a fifth connector, a sixth connector and an eleventh valve. The fifth connector can connect the tenth valve to a fourth valve. The forth valve can connect the fifth connector, a third wash line, and the first module. The third wash line can connect the fourth valve to a third recharger connector. The sixth connector can connect the tenth valve to a fifth valve. The fifth valve can connect the sixth connector, a fourth wash line and the second module. The fourth wash line can connect a fourth recharger connector. The eleventh valve can connect the fourth connector, a seventh connector, an eighth connector and a twelfth valve. The seventh connector can connect the eleventh valve to a sixth valve. The sixth valve can connect the seventh connector, a fifth wash line and the third module. The fifth wash line can connect a fifth recharger connector. The eighth connector can connect the eleventh valve to a seventh valve. The seventh valve can connect the eighth connector, a sixth wash line and the fourth module. The sixth wash line can connect the seventh valve to a sixth recharger connector. The twelfth valve can connect the fourth connector, a ninth connector and a tenth connector. The ninth connector can connect the twelfth valve to an eighth valve. The eighth valve can connect the ninth connector, a seventh wash line and the third module. The seventh wash line can connect the eighth valve to a seventh recharger connector. The tenth connector can connect the twelfth valve to a ninth valve. The ninth valve can connect the tenth connector, an eighth wash line and the fourth module. The eighth wash line can connect the ninth valve to an eighth recharger connector.

In another embodiment, a first and second module can be positioned parallel to one another, a third and fourth module can be positioned parallel to one another, and the first and second modules can be in series with the third and fourth modules, respectively. A first valve can connect a first, second, third and fourth connector. The second connector can connect the first valve to a second valve. The second valve can connect the second connector, a first wash line and the first module. The first wash line can connect the second valve to a first recharger connector. The third connector can connect the first valve to a third valve. The third valve can connect the third connector, a second wash line and the second module. The second wash line can connect the third valve to a second recharger connector. The fourth connector can connect the first valve to a twelfth valve. The twelfth valve can connect the fourth connector, a fifth connector, a sixth connector and a thirteenth valve. The fifth connector can connect the twelfth valve to a sixth valve. The sixth valve can connect the fifth connector, a fourth valve and an eighth valve. The fourth valve can connect the sixth valve, a third wash line and the first module. The third wash line can connect the fourth valve to a third recharger connector. The sixth connector can connect the twelfth valve to a seventh valve. The seventh valve can connect the sixth connector, a ninth valve and a fifth valve. The fifth valve can connect the seventh valve, a fourth wash line and the second module. The fourth wash line can connect the fifth valve to a fourth recharger connector. The eighth valve can connect the sixth valve, a fifth wash line and the third module. The fifth wash line can connect the eighth valve to a fifth recharger connector. The ninth valve can connect the seventh valve, a sixth wash line and the fourth module. The sixth wash line can connect the ninth valve to a sixth recharger connector. The thirteenth valve can connect the fourth connector, a seventh connector and an eighth connector. The seventh connector can connect the thirteenth valve to a tenth valve. The tenth valve can connect the seventh connector, a seventh wash line and the third module. The seventh wash line can connect the tenth valve to a seventh recharger connector. The eighth connector can connect the thirteenth valve to an eleventh valve. The eleventh valve can connect the eighth connector, an eighth wash line and the fourth module. The eighth wash line can connect the eleventh valve to an eighth recharger connector.

In another embodiment, a first and second module can be positioned parallel to one another, a third and fourth module can be positioned parallel to one another, a fifth and sixth module can positioned parallel to one another and the first and second modules can be in series with the third and fourth modules, and the third and fourth modules can be in series with the fifth and sixth modules, respectively. A first valve can connect a first, second, third and fourth connector. The second connector can connect the first valve to a second valve. The second valve can connect the second connector, a first wash line and the first module. The first wash line can connect the second valve to a first recharger connector. The third connector can connect the first valve to a third valve. The third valve can connect the third connector, a second wash line, and the second module. The second wash line can connect the third valve to a second recharger connector. The fourth connector can connect the first valve to a fourteenth valve. The fourteenth valve can connect the fourth connector, a fifth connector, a sixth connector and a fifteenth valve. The fifth connector can connect the fourteenth valve to a fourth valve. The forth valve can connect the fifth connector, a third wash line, and the first module. The third wash line can connect the fourth valve to a third recharger connector. The sixth connector can connect the fourteenth valve to a fifth valve. The fifth valve can connect the sixth connector, a fourth wash line and the second module. The fourth wash line can connect a fourth recharger connector. The fifteenth valve can connect the fourth connector, a seventh connector, an eighth connector and a sixteenth valve. The seventh connector can connect the fifteenth valve to a sixth valve. The sixth valve can connect the seventh connector, a fifth wash line and the third module. The fifth wash line can connect a fifth recharger connector. The eighth connector can connect the fifteenth valve to a seventh valve. The seventh valve can connect the eighth connector, a sixth wash line and the fourth module. The sixth wash line can connect the seventh valve to a sixth recharger connector. The sixteenth valve can connect the fourth connector, a ninth connector, a tenth connector and a seventeenth valve. The ninth connector can connect the sixteenth valve to an eighth valve. The eighth valve can connect the ninth connector, a seventh wash line and the third module. The seventh wash line can connect the eighth valve to a seventh recharger connector. The tenth connector can connect the sixteenth valve to a ninth valve. The ninth valve can connect the tenth connector, an eighth wash line and the fourth module. The eighth wash line can connect the ninth valve to an eighth recharger connector. The seventeenth valve can connect the fourth connector, an eleventh connector, a twelfth connector and an eighteenth valve. The eleventh connector can connect the seventeenth valve to a tenth valve. The tenth valve can connect the eleventh connector, a ninth wash line and the fifth module. The ninth wash line can connect the tenth valve to a ninth recharger connector. The twelfth connector can connect the seventeenth valve to an eleventh valve. The eleventh valve can connect the twelfth connector, a tenth wash line and the sixth module. The tenth wash line can connect the eleventh valve to a tenth recharger connector. The eighteenth valve can connect the fourth connector, a thirteenth connector and a fourteenth connector. The thirteenth connector can connect the eighteenth valve to a twelfth valve. The twelfth valve can connect the thirteenth connector, an eleventh wash line and the fifth module. The eleventh wash line can connect the twelfth valve to an eleventh recharger connector. The fourteenth connector can connect the eighteenth valve to a thirteenth valve. The thirteenth valve can connect the fourteenth connector, a twelfth wash line and the sixth module. The twelfth wash line can connect the thirteenth valve and a twelfth recharger connector.

In another embodiment, the sorbent cartridge can comprise at least one reusable module having one or more connectors.

In another embodiment, the cartridge can comprise at least one non-reusable module.

In another embodiment the at least one reusable module can contain sorbent material.

In another embodiment the at least one reusable module can contain multiple sorbent materials.

In another embodiment the at least one non-reusable module can contain sorbent material.

In another embodiment the at least one non-reusable module can contain multiple sorbent materials.

In any embodiment the connectors may be quick-connect, twist lock, push-on or threaded fitting.

In any embodiment the connectors may comprise a length of tubing and a valve assembly.

In one embodiment, the sorbent material in the reusable module may be selected from a group comprising zirconium phosphate, hydrous zirconium oxide, activated carbon, alumina, urease, and ion exchange resin. In any embodiment, the ion exchange resin can be selected to only remove calcium and magnesium ions by using a chelating ion exchange resin. The respective layers can be formed into any combination of layers without restriction.

In one embodiment, the sorbent material in the non-reusable module may be selected from a group comprising zirconium phosphate, hydrous zirconium oxide, activated carbon, alumina, urease, and ion exchange resin. In any embodiment, the ion exchange resin can be selected to only remove calcium and magnesium ions by using a chelating ion exchange resin. The respective layers can be formed into any combination of layers without restriction.

In one embodiment, the reusable module can be detachable from the sorbent cartridge.

In another embodiment, the reusable module can be recyclable.

In any embodiment, the modules may have a barcode or other identification system.

In any embodiment, the connectors may have an access point for a sensor.

The invention is also directed to a fluid circuit. In one embodiment the circuit can have at least two modules connected by one or more connectors in parallel. The circuit can have an operational line directing flow along the connectors and through the modules. The circuit can have at least one wash line fluidly connecting one or more connectors to a recharger. The fluid circuit can also have at least one bypass line to bypass at least one module and operational line.

The invention is also directed towards a method of recharging a sorbent. In one embodiment, this method can include connecting at least a first and second module in parallel with one or more connectors. The method can include fluidly connecting at least one connector to a wash line. The wash line can be fluidly connected to a recharger. The method can include fluidly connecting at least one connector to a bypass line. The bypass line can divert flow from the connector to bypass at least one module. The method can include connecting one or more valves to the connectors at junctions between the modules, bypass lines and/or wash lines. The method can include selectively opening and closing the valves to direct the flow through the connectors, modules, bypass lines and/or wash lines.

In another embodiment the method can comprise an either two-way, three-way, or four-way, or a combination thereof, valve positioned on a connector before the first module, the valve connecting the connector, a wash line and the second module. The valve can be open to the wash line and closed to the connector and the second module such that flow is directed to a recharger.

In another embodiment the method can comprise an either two-way, three-way, or four-way, or a combination thereof, valve positioned on a connector before the first module, the valve connecting the connector, a wash line and the second module. The valve can be open to the wash line and connector and closed to the second module such that flow is directed to a recharger.

In another embodiment, the method can comprise an either two-way, three-way, or four-way, or a combination thereof, valve positioned on a connector before the first module, the valve connecting the connector, a wash line and the second module. The valve can be open to the wash line and connector, and closed to the second module such that flow circulates between the first module and the recharger, but wherein flow cannot continue from the first module to the second module.

In another embodiment, the method can comprise an either two-way, three-way, or four-way, or a combination thereof, valve positioned on a connector before the first module, the valve connecting the connector, a wash line and the second module. The valve can be open to the second module, and closed to the wash line and the connector, such that flow is directed to the second module.

In another embodiment, the method can comprise an either two-way, three-way, or four-way, or a combination thereof, valve positioned on a connector before the first module, the valve connecting the connector, a wash line and the second module. The valve can be open to the connector, and closed to the second module and wash lines, such that flow is directed through the connector and through the first module.

In another embodiment a pump can be attached to the recharger or wash line.

In another embodiment, a gas, such as argon gas, nitrogen gas and air, can be used to blow out the module.

In another embodiment the wash lines can be subdivided into a top and bottom line.

In one embodiment the top line can be a liquid line and the bottom line can be a gas line.

In another embodiment the top line can be a gas line and the bottom line can be a liquid line.

In another embodiment the top and bottom lines can both be liquid lines.

In any embodiment, the at least two modules can be part of a controlled compliant dialysis circuit.

In any embodiment the valves can be operated under control of a programmable controller or computer system to regulate flow into, out of, and between modules.

In any embodiment, the fluid flow through the valves can be sensed by a photocell or other flow sensing and/or measuring apparatus.

In any embodiment a control pump can be utilized to circulate fluid in the fluid flow path.

In another embodiment, the multiple sorbent materials may be mixed together.

In another embodiment, the sorbent cartridge can have a first and second module positioned parallel to one another, a third and fourth module positioned parallel to one another, and a fifth and sixth module positioned parallel to one another. The first and second modules can be in series with the third and fourth modules, and the third and fourth modules can be in series with the fifth and sixth modules, respectively. The first and second modules can be fluidly connected to a first set of one or more valves positioned on a first set of one or more connectors before the first and second modules, such that fluid may be directed into either the first or second module. A bypass line can be fluidly connected to the first set of one or more valves such that fluid can bypass both the first and second module. A first recharger connector can be fluidly connected to the first set of one or more valves such that fluid may be directed from the first recharger connector to either the first or second module. The first module, second module, and bypass line can be fluidly connected to a second set of one or more valves positioned on a second set of one or more connectors after the first and second modules and before the third and fourth modules, such that fluid may be directed from the first or second module into either the third or fourth module. The bypass line can be fluidly connected to the second set of one or more valves such that fluid can bypass both the third and fourth module. A second recharger connector can be fluidly connected to the second set of one or more valves such that fluid may be directed from the second recharger connector to either the third or fourth module. The third module, fourth module, and bypass line can be fluidly connected to a third set of one or more valves positioned on a third set of one or more connectors after the third and fourth modules and before the fifth and sixth modules, such that fluid may be directed from the third or fourth module into either the fifth or sixth module. The bypass line can be fluidly connected to the third set of one or more valves such that fluid can bypass both the fifth and sixth module. A third recharger connector can be fluidly connected to the third set of one or more valves such that fluid may be directed from the third recharger connector to either the fifth or sixth module.

In another embodiment, a first and second module can positioned parallel to one another, a third and fourth module can be positioned parallel to one another, and the first and second modules can be in series with the third and fourth modules, respectively. The first and second modules can be fluidly connected to a first set of one or more valves positioned on a first set of one or more connectors before the first and second modules, such that fluid may be directed into either the first or second module. A bypass line can be fluidly connected to the first set of one or more valves such that fluid can bypass both the first and second module. A first recharger connector can be fluidly connected to the first set of one or more valves such that fluid may be directed from the first recharger connector to either the first or second module. The first module, second module, and bypass line can be fluidly connected to a second set of one or more valves positioned on a second set of one or more connectors after the first and second modules and before the third and fourth modules, such that fluid may be directed from the first or second module into either the third or fourth module. The bypass line can be fluidly connected to the second set of one or more valves such that fluid can bypass both the third and fourth module. A second recharger connector can be fluidly connected to the second set of one or more valves such that fluid may be directed from the second recharger connector to either the third or fourth module.

In another embodiment, a first module can be positioned in series before a second and third module. The second and third module can be positioned parallel to one another. The first module can be connected to a set of one or more connectors positioned after the first module and before the second and third modules. A set of one or more valves can be positioned on the set of one or more connectors such that fluid may be directed into either the second or third module. A bypass line can be fluidly connected to the set of one or more valves such that fluid can bypass both the second and third module. A recharger connector can be fluidly connected to the set of one or more valves such that fluid may be directed from the recharger connector to either the second or third module.

In another embodiment, a first and second module can be positioned parallel to one another, a third and fourth module can be positioned parallel to one another, and a fifth and sixth module can be positioned parallel to one another. The first and second modules n be in series with the third and fourth modules, and the third and fourth modules can be in series with the fifth and sixth modules, respectively. The first and second modules can be fluidly connected to a first set of one or more valves positioned on a first set of one or more connectors before the first and second modules, such that fluid may be directed into either the first or second module. A bypass line can be fluidly connected to the first set of one or more valves such that fluid can bypass both the first and second module. The first module, second module, and bypass line can be fluidly connected to a second set of one or more valves positioned on a second set of one or more connectors after the first and second modules and before the third and fourth modules, such that fluid may be directed from the first or second module into either the third or fourth module. The bypass line can be fluidly connected to the second set of one or more valves such that fluid can bypass both the third and fourth module. The third module, fourth module, and bypass line can be fluidly connected to a third set of one or more valves positioned on a third set of one or more connectors after the third and fourth modules and before the fifth and sixth modules, such that fluid may be directed from the third or fourth module into either the fifth or sixth module. The bypass line can be fluidly connected to the third set of one or more valves such that fluid can bypass both the fifth and sixth module.

In another embodiment, a first and second module can be positioned parallel to one another, a third and fourth module can be positioned parallel to one another, and the first and second modules can be in series with the third and fourth modules, respectively. The first and second modules can be fluidly connected to a first set of one or more valves positioned on a first set of one or more connectors before the first and second modules, such that fluid may be directed into either the first or second module. A bypass line can be fluidly connected to the first set of one or more valves such that fluid can bypass both the first and second module. The first module, second module, and bypass line can be fluidly connected to a second set of one or more valves positioned on a second set of one or more connectors after the first and second modules and before the third and fourth modules, such that fluid may be directed from the first or second module into either the third or fourth module. The bypass line can be fluidly connected to the second set of one or more valves such that fluid can bypass both the third and fourth module.

In another embodiment, a first module can be positioned in series before a second and third module. The second and third module can be positioned parallel to one another. The first module can be connected to a set of one or more connectors positioned after the first module and before the second and third modules. A set of one or more valves can be positioned on the set of one or more connectors such that fluid may be directed into either the second or third module. A bypass line can be fluidly connected to the set of one or more valves such that fluid can bypass both the second and third module.

DETAILED DESCRIPTION OF THE INVENTION

Figure 1:
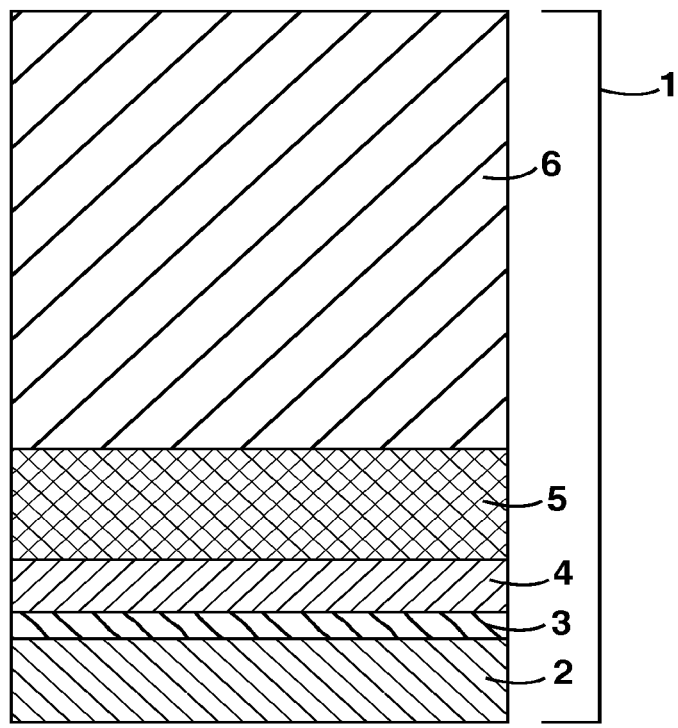
FIG. 1 shows a sorbent cartridge containing activated carbon, hydrous zirconium oxide, urease, alumina, and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Blow out" refers to the process of passing a gas through a connection line or a module.

"Bypass line" refers to a line, connected to the main line, through which fluid or gas may alternatively flow.

The term "cartridge" refers to any container designed to contain a powder, liquid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "cation concentrate reservoir" refers to an object having or holding a substance that is comprised of at least one cation, for example calcium, magnesium, or potassium ions.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein liquid or gas can flow from one of the components, through the connector, to another component. It will be understood that the connector provides for a fluid connection in its broadest sense and can include any type of tubing, fluid or gas passageway, or conduit between any one or more components of the invention.

The term "consisting essentially of" includes whatever follows the term "consisting essentially of" and additional elements, structures, acts or features that do not affect the basic operation of the apparatus, structure or method described.

The term "consisting of" includes and is limited to whatever follows the phrase "consisting of" Thus, the phrase indicates that the limited elements are required or mandatory and that no other elements may be present.

The term "container" as used herein in the context of a controlled compliant circuit is a receptacle that may be flexible or inflexible for holding any fluid or solid, such as for example a spent dialysate fluid, or a sodium chloride or sodium bicarbonate solution or solid, or the like.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path," "controlled compliant dialysate flow path" and "controlled compliant solution flow path" refer to flow paths operating within a controlled compliant system having the characteristic of controlled compliance, or of being controlled compliant as defined herein.

A "control pump" is an apparatus capable of moving fluid through a system at a specific rate. The term "control pump" can include for example an "ultrafiltrate pump," which is a pump that is operable to pump fluid bi-directionally to actively control the transfer of fluid volume into or out of a compartment or circuit.

A "controller," "control unit," "processor," or "microprocessor" is a device which monitors and affects the operational conditions of a given system. The operational conditions are typically referred to as output variables of the system wherein the output variables can be affected by adjusting certain input variables.

A "control system" consists of combinations of components that act together to maintain a system to a desired set of performance specifications. The control system can use processors, memory and computer components configured to interoperate to maintain the desired performance specifications. It can also include fluid or gas control components and solute control components as known within the art to maintain the performance specifications.

A "control valve" is a valve for controlling the movement of a liquid or a gas. When the control valve directs the movement of gas, the "control valve" can open or close to regulate the movement of gas from a high pressure gas source to a lower pressure.

A "degasser" is a component that is capable of removing dissolved and undissolved gasses from fluids.

The term "detachable" or "detached" relates to any component of the present invention that can be separated from a system, module, cartridge or any component of the invention. "Detachable" can also refer to a component that can be taken out of a larger system. In certain instances, the components can be detached with minimal time or effort, but in other instances can require additional effort. The detached component can be optionally reattached to the system, module, cartridge or other component. A detachable module can often be part of a reusable module as defined herein.

"Dialysate" is the fluid that passes through the dialyzer and does not appreciably pass through the membrane into the blood flow.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Disposable" refers to a component that is intended to be used for a certain period of time or until no longer useful, and can then be removed from the system and discarded.

The term "extracorporeal," as used herein generally means situated or occurring outside the body.

The term "extracorporeal circuit" or "extracorporeal flow path" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

"Flow" refers to the movement of a liquid or a gas.

A "flow sensing apparatus" or "flow measuring apparatus" is an apparatus capable of measuring the flow of liquid or gas within a specific area.

A "fluid" is a liquid substance.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point in its broadest sense without limitation as to form or type of fluid being transferred between any two points. For example, the two points can be within or between any one or more of compartments, modules, systems, components, and recharger connectors, all of any type, form or configuration.

"Infusate" is a solution of one or more salts for the adjustment of the composition of a dialysate.

The term "in-line" refers to state in which a module or set of modules is fluidly connected to dialysis machine, dialysis flow path or dialysis circuit. Dialysis can be on-going, paused or stopped during the in-line state wherein in-line only refers to the state of the modules being fluidly connected to the dialysis machine, dialysis flow path or dialysis circuit.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. It will be understood that the designation of "first," "second," "third," etc. does not refer to the respective placement of the module in the direction of fluid or gas flow, and merely serves to distinguish one module from another unless otherwise indicated.

The term "non-reusable" refers to a component that cannot be reused in the component's current state. In certain instances, the term non-reusable can include the concept of being disposable, but is not necessarily limited to just being disposable.

The term "off-line" refers to a state in which a module or set of modules is fluidly disconnected from a dialysis machine, dialysis flow path or dialysis circuit. Dialysis can be on-going, paused or stopped during the off-line state wherein off-line only refers to the state of the modules being fluidly disconnected from the dialysis machine, dialysis flow path or dialysis circuit. The off-line state can also include a process whereby the module or set of modules is being recharged as defined herein.

The term "online" refer to state in which a module or set of modules is fluidly connected to dialysis machine, dialysis flow path or dialysis circuit. Dialysis can be on-going, paused or stopped during the online state wherein online only refers to the state of the modules being fluidly connected to the dialysis machine, dialysis flow path or dialysis circuit.

An "operational line" or "line" is a passageway, conduit or connector that directs fluid or gas in a path used while the system is in operation.

The terms "pathway," "conveyance pathway," "fluid flow path," and "flow path" refer to the route through which a fluid or gas, such as dialysate or blood, travels, or the route an inert gas travels.

A "photocell" is a sensor capable of measuring light or other electromagnetic radiation.

The terms "pressure meter" and "pressure sensor" refer to a device for measuring the pressure of a gas or liquid in a vessel or container.

A "pressure valve" is a valve wherein, if the pressure of the fluid or gas passing the valve reaches a certain level, the valve will open to allow fluid or gas to pass through.

The term "pump" refers to any device that causes the movement of fluids or gases by the application of suction or pressure.

A "push-on fitting" is a fitting for connecting two components wherein the components may be connected by applying pressure to the base of the fitting attached to the components.

A "quick connect fitting" is a fitting for connecting two components wherein the male portion of the fitting contains flexible flanges extending outward with a portion on the end of the flange extending further outward, and the female portion of the fitting contains an internal ridge so that when connected, the outward extending portion of the flange sits under the ridge. By applying pressure, the flexible flange can be forced inward, past the ridge, enabling easy removal.

A "recharger" is a component that is capable of recharging spent sorbent material to or near its original state or usable capacity. A recharger may be part of the dialysis system, or may be separate from the rest of the system. If the recharger is separate from the rest of the dialysis system, the term may include a separate facility where the spent sorbent material is sent to be returned to, or near, its original state. A "recharger connector" or "recharger node" is a connector that fluidly connects a recharger to another component.

"Recharging" refers to the process of treating a material so as to put the material back in condition for use in sorbent dialysis. In one non-limiting example, the material can be a spent sorbent material where upon the spent sorbent material undergoing "recharging," the sorbent material can then be said to be "recharged."

The term "recyclable" refers to material that can be reused.

"Reusable" refers in one instance to a material that can be used more than one time, possibly with treatment or recharging of the material between uses. In one non-limiting example, the material can be a spent sorbent material. Reusable may also refer to a sorbent cartridge that contains a sorbent material that can be recharged by recharging the sorbent material(s) contained within the sorbent cartridge.

A "sensor" is a component capable of determining the states of one or more variables in a system.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent materials" are materials that are capable of removing specific solutes from solution, such as urea.

"Spent dialysate" is a dialysate that has contacted with blood through a dialysis membrane and contains one or more impurity, waste species, or waste substance, such as urea.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

"Tap water" refers to water obtained through piping from a water supply without additional treatment.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

"Uremic toxins" are toxins carried in the blood supply normally removed in the kidneys.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "wash line" is a line that directs fluid between a recharger and a module.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "water source" refers to a source from which potable or not potable water can be obtained.

The term "waste species," "waste products," "waste," or "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

Sorbent Dialysis

Sorbent dialysis allows for dialysis with a small volume of dialysate, creating many advantages. In sorbent dialysis, spent dialysate, containing toxins removed from the blood of the patient, is passed through a sorbent cartridge. The sorbent cartridge of the invention can contain sorbent materials that selectively remove specific toxins from the spent dialysate, either completely or by replacing them with non-toxic material. This process converts the spent dialysate into clean dialysate, which can then be redirected back to the dialyzer.

Modular sorbent cartridges, wherein each module contains select sorbent materials, can be useful in sorbent dialysis. This modular design critically allows for certain portions of the sorbent cartridge to be discarded, refilled, recycled or recharged. In certain embodiments, the sorbent materials can be structured into layers and/or intermixed. In particular, the modules can have the sorbent materials either intermixed or in layers wherein any combination of intermixed and layered modules can be used interchangeably together.

One non-limiting, exemplary sorbent cartridge is shown in FIG. 1. Spent dialysate can flow from the bottom of the sorbent cartridge 1 to the top of the cartridge. The first sorbent material the spent dialysate (or fluid) contacts can be activated carbon 2. Activated carbon will remove nonionic toxins from the fluid by adsorption. Creatinine, glucose, uric acid, □2-microglobulin and other non-ionic toxins, except urea, can be adsorbed onto the activated carbon, removing those toxins from the fluid. Other non-ionic toxins will also be removed by the activated carbon. The dialysate (or fluid) then continues through the sorbent cartridge to the hydrous zirconium oxide layer 3. The hydrous zirconium oxide layer can remove phosphate and fluoride anions, exchanging them for acetate anions. The fluid can continue to move through the sorbent cartridge into the alumina/urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge, it reaches alumina layer 5. Alumina layer 5 can remove any remaining phosphate ions from the fluid and help retain urease within the sorbent cartridge, and in certain configurations this layer can exchange urea for ammonium and other components. The last layer through which the fluid travels can be zirconium phosphate layer 6. In the zirconium phosphate layer 6, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the layer. The ratio of sodium to hydrogen ions released depends on the ratio originally present in the zirconium phosphate layer 6, and is therefore controllable. The result of the fluid passing through the sorbent cartridge is that the fluid can be regenerated and form clean dialysate that can be safely passed back through a dialyzer to a patient. In any embodiment, potassium, calcium and magnesium can be added to the clean dialysate to replace any ions which were removed by the sorbent cartridge. Those ions can be added and/or controlled via an infusate system that can be positioned on the section of the fluid flow path after the sorbent cartridge.

Figure 2:
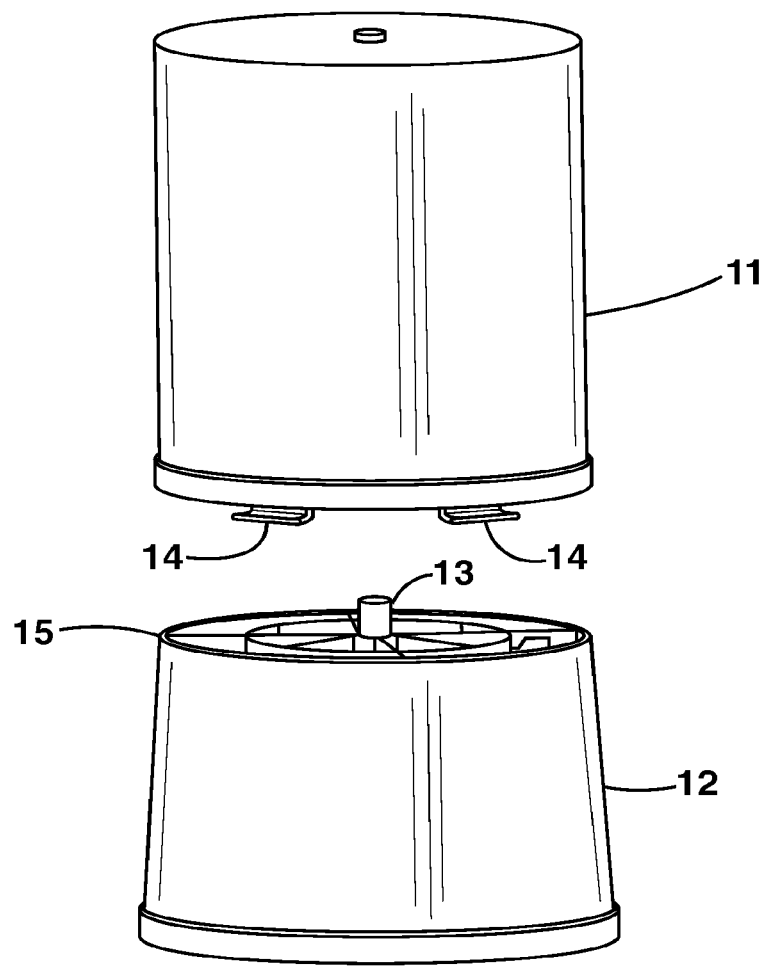
FIG. 2 shows a modular sorbent cartridge with two modules.

Given the cost of the sorbent cartridges and sorbent materials, it would be advantageous if parts of the cartridge could be reused or recharged. The present invention relates to a sorbent cartridge which includes at least one reusable module. As shown in FIG. 2, a reusable module 11 can be fluidly attached to a non-reusable module 12 by a connector 13 with the use of latches 14. The latches 14 can be integrally formed as part of the reusable module 11, or non-reusable module 12. Alternatively, they may be a separate component that must be attached to the module 11. The latches 14 operate to hold reusable module 11 and non-reusable module 12 together, and may be made out of any material known to those of ordinary skill. The latch members 14 can be mated to an annular connection ring 15 disposed on the circumference of module 12. One or more engagement members can be disposed inside the annular connection ring 15 to engage the latches 14 when positioned relative to each other using a radial motion. Such engagement can cause a rigid connection between the reusable module 11 and the non-reusable module 12. Other known locking or fastening mechanisms known to those of ordinary skill that can effectuate rapid and effective connections between two components are contemplated by the invention. Although only cylindrical modules are shown, it will be understood that modules of any shape such as rectangular, conical, triangular, etc. are contemplated by the present invention with a correspondent fastening mechanism. It will be understood that different combinations of reusable and non-reusable modules can be combined together. In certain embodiments, both modules may be reusable or both may be non-reusable. Moreover, any one of the modules can be detachable from each other or from a casing forming the body of the sorbent cartridge.

The modules can be standardized components that are interchangeable with other modules and easily assembled. For example, the latches 14 in FIG. 2 allow for a simple, twist-lock between two modules. The twist lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 14 to disengage from the engagement members. In other examples, the modules can be disengaged by simply rotating the modules relative to each other.

In certain embodiments, each module can function as a sorbent cartridge independently. In other embodiments, at least two modules can cooperate together when engaged to each other using, for example the latches 14 in FIG. 2 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

In certain embodiments, the connector 13 can be formed as part of the reusable module 11 and non-reusable module 12 and need not be a separate component that must be attached to the module 12. Rather, the connector 13 can be molded as part of the reusable module 11 and non-reusable module 12. The connector can be a combination of female and male connectors on a module. For example, a female connector can be disposed on one module, and a male connector on the other to form one connector 13 (not shown). In other embodiments, the connector can be affixed by mechanical means, glued or rigidly interfaced to the modules 11 and 12. In any embodiment, the connector 13 allows fluid to flow from the non-reusable module, through the connector, into the reusable module. Alternatively, the connector 13 is not a part of either the non-reusable module 12 or reusable module 11 but can be a separate component such as tubing. It will be understood that the connector 13 is defined in its broadest sense and encompasses any fluid connection between two points.

In any embodiment, one or more fluid connectors can be arranged between any module of the invention, and one or more such fluid connectors can be provided in any of the described configurations herein. For example, a reusable or non-reusable module can have any number of connectors such as 1, 2, 3, 4, 5, or more. The spacing and distribution of the fluid connectors on the module can be positioned to enable and/or increase flow of fluid between the modules. In one example, the fluid connectors can be spaced equidistant from each other or may be located axially or radially. The sorbent cartridge can also have one or more modules each having any number of fluid connectors. In contrast to known sorbent cartridges having a unitary design in which sorbent materials are arranged in layers without any connectors between such layers, the fluid connectors of the present invention allow for controlled fluid or gas flow to any particular sorbent or combination of sorbent materials. The fluid connectors also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. It will be understood that the fluid connectors of the invention can be critical because the connectors control the order of sorbent materials to which a fluid or gas is exposed, the delivery of fluid or gas to a particular sorbent or combination of sorbent materials, and the flow and rate of flow of a fluid or gas to various sorbents and combinations of sorbent material.

In one aspect of the invention, it will be understood that the present invention contemplates at least two modules that fit together, which is distinct from known dialysis systems requiring separate housings containing sorbent materials that do not form a unitary sorbent cartridge for ready attachment or insertion into a dialysis machine. A unitary sorbent cartridge of the present invention contains each one of the sorbent materials described herein including cation and anion exchange resins inside the sorbent cartridge. In other words, the cation and anion exchange resins (or other sorbent materials) are not separated into another housing outside the sorbent cartridge. Although the individual sorbent materials of the present invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the present invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the present sorbent cartridge can therefore be easier to recycle, recharge, dispose of, service and remove from a dialysis machine. In certain embodiments, the unitary design can also provide for a compact design that can be used in a portable dialysis machine. Further, manufacturability is benefited by the unitary design.

In any embodiment, the fluid connector can be a quick-connect, twist-lock, push-on, or threaded fitting. Other forms of such connection known to those of ordinary skill in the art are also contemplated by the present invention. Additionally, the connector can comprise a length of tubing and a valve assembly. In certain embodiments, the connector can be manually assembled to connect any component or assembly of the invention. The connector can also be used to rigidly connect any one of the modules to a recharger as defined herein when a separate fastening mechanism is not provided.

Figure 19:
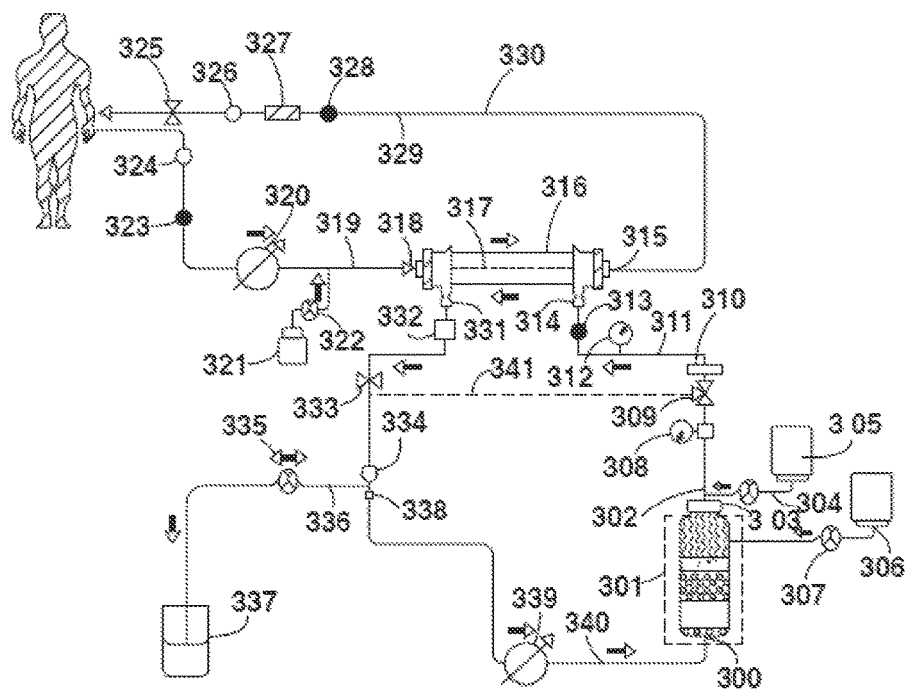
FIG. 19 shows the use of a sorbent cartridge in a controlled compliance dialysis circuit.

In any embodiment of the invention, at least one module can be in fluid communication with a controlled compliant dialysis circuit. A non-limiting example of a controlled compliant dialysis circuit is shown in FIG. 19 as disclosed in U.S. patent application Ser. No. 13/565,733, the contents of which are incorporated herein in their entirety. As shown in the controlled compliant dialysis circuit of FIG. 19, the patient's blood is circulated through an extracorporeal circuit 330. The portion of the extracorporeal circuit 330 that contains drawn blood from the patient can be referred to as the arterial line 319, which by convention is understood to mean a line for transporting blood from the patient regardless of whether blood is drawn from an artery or vein of the patient. Similarly, the portion that returns blood to the patient can be referred to as the venous line 329. In certain embodiments, the arterial line 319 and the venous line 329 connect with one or more veins of the patient. Locomotive power for moving the blood through the extracorporeal circuit 330 is provided by a blood pump 320, which is typically located along the arterial 319 line. Valve 325 can be placed on venous line 329. Blood is typically conveyed through the extracorporeal circuit 330 at a rate of 50 to 600 mL/min and can be adjusted by a controller to any required rate suitable for a procedure performed by the invention. Blood pump 320 can be a peristaltic pump, although those skilled in the art will readily understand that other types of pumps can be used including diaphragm pumps, centrifugal pumps, and shuttle pumps. In certain embodiments, the blood pump 320 conveys blood through the dialyzer 316 where the blood is contacted with a blood side of a high permeability dialysis membrane 317. Blood enters the dialyzer 316 through a blood inlet 318 and exits through a blood outlet 315. The pressure of the blood prior to the blood pump 320 is measured by a pressure meter 323 and post dialyzer 316 by a pressure meter 328. The pressure at pressure meter 323 provides an indication of the adequacy of the blood flow into the circuit where increased vacuum is an indication of a less adequate access flow. The pressure indication at pressure meter 328 can serve to detect obstructions in the venous bloodline. Additional pressure meter 313 can be located after blood outlet 315. An air trap 327 is placed along the extracorporeal circuit 330 to prevent the introduction of air into the circulatory system of the patient. The air trap 327 is not limited to a particular design. Typical air traps employ a hydrophobic membrane that allows air to be separated from an air-liquid mixture by allowing air to pass through the membrane and retaining water-based fluids. Alternatively the air trap 327 can be run full, where a pressure meter can use a flexible impermeable membrane to transmit pressure pulses to a pressure transducer such that there is no direct air blood interface. Air-fluid detectors 324 and 326 are present to confirm that air is not present in the extracorporeal circuit 330, and additional air-fluid detector 334 can be present in the dialysis circuit 340. Air fluid detectors 324, 326 and 334 can be ultrasonic sensors that can detect a change in solution density or scattering due to the presence of air or air bubbles.

During the course of conveyance of blood along the extracorporeal circuit 330, heparin or other anticoagulant is added to the blood to prevent clotting of blood within the dialyzer 316 or blood conveyance pathway/extracorporeal circuit 330. Heparin or another anticoagulant is added from an anticoagulant container 321 at a metered rate using an anticoagulant pump 322. The anticoagulant pump 322 can be any pump capable of accurately metering heparin.

Dialysate within the system is conveyed through one of a first dialysate pathway 311 in the dialysate circuit, which carries dialysate to the dialyzer 316, or a second bypass pathway 341 shown in a dashed line, which serves to bypass the dialyzer 316. The dialysis circuit can include a pair of quick connectors 338. The first and second pathways 311 and 341 have one or more conduits for conveying the dialysate. Access to the second bypass pathway 341 is controlled by valve 309. It is understood by one skilled in the art that three-way valve 309 can be replaced with a two-way valve with the same result to control the flow through the dialyzer 316 or bypass pathway 341. The first dialysate pathway 311, the second bypass pathway 341, and residual volume in the dialyzer 316 including conduits for conveying the dialysate together form a dialysis circuit 340 that houses the circulating volume of the dialysate present in the system. It is understood by one skilled in the art that three-way valve 309 could be replaced with two-way valves with the same result to control the flow through the dialyzer or bypass loop.

Dialysate that is conveyed through the dialyzer 316 on the dialysate side of the dialysis membrane 317 picks up waste produces from the blood, including urea, by diffusion, hemofiltration or hemodiafiltration. Dialysate enters the dialyzer at a dialysate inlet end 314 and exits at an outlet end 331. The dialysate exiting the dialyzer 316 passes through a blood leak detector 332 that can determine the presence of blood in the dialysate indicating a breach in the dialysis membrane 317. Flow of dialysate from the dialyzer 316 can be stopped or controlled through the operation of valve 333 as well as to prevent the backup of dialysate into the dialyzer 316. The dialysate is conveyed through a sorbent cartridge 301 to remove waste products before being re-conveyed through the dialyzer 316. The dialysate enters the sorbent cartridge 301 at a dialysate inlet end 300 and exits at an outlet end 302. Refreshed dialysate exiting an outlet end 302 of the sorbent cartridge 301 can be monitored by a conductivity meter 308. Additional conductivity meter 312 can be present. Optionally, the dialysate can be filtered through a microbial filter 310. An air trap 303 can be positioned before or after outlet end 302 to remove gasses introduced into the dialysate by the sorbent cartridge 301. The volume of actively circulating dialysate is determined by the total void volume of the conduits and the sorbent cartridge 301 forming the dialysis circuit 340. The void volumes of the conduits and of the sorbent cartridge 301 forming the dialysis circuit 340 have a non-expandable or substantially inflexible volume.

The total void volume of the conduits having a substantially inflexible volume prevents the passive inflow and outflow of fluid volume due to pressure changes that can occur over the course of treatment. This results in a benefit because not all of the pressure changes during treatment are under precise control by a user or operator. A controlled compliance dialysis circuit is achieved by actively controlling the inflow (influx) and outflow (efflux) of fluid to and from the dialysis circuit 340 and the extracorporeal circuit 330. In this manner, the volume of fluid crossing the dialysate membrane 317 is under direct control and can be accurately determined.

The controlled compliance dialysis circuit can be accurately controlled to precisely remove or add fluid to the dialysis circuit. Due to the substantially inflexible void volume of the conduits, the sorbent cartridge 301 and other components of the dialysis circuit 340, the net movement of fluid over any time interval across the dialysate membrane can be accurately controlled by creating a means to accurately introduce or remove fluid from the patient. This capability is used to enhance the convective clearance of the system while controlling the net fluid removed from the patient.

As shown in FIG. 19, the dialysate is moved along the dialysis circuit 340 by a dialysate pump 339. When the control pump 335 is not operating, fluid along the length of the dialysis circuit 340 flows at a rate determined by the dialysate pump 339. When the control pump 335 is operating, fluid exiting the dialyzer 316 and traveling toward the conduit 336 is flowing at a rate that is the combination of the rates of the control pump 335 and the dialysate pump 339. However, the fluid traveling from the entry point of conduit 336 into the dialysis circuit 340 to the dialyzer 316 is traveling at the rate of the dialysate pump 339. As such, the rate of fluid traveling to the dialyzer 316 is not affected by the operation of the control pump 335. The dialysate pump can be operated at a rate from about 10 to about 400 mL/min, the specific rate being dependent on the rate of the blood pump 320 at the desired contact time with the dialysis membrane 317 to achieve diffusion of impurities from blood to the dialysate. The rate of the dialysate pump 339 and the blood pump 320 can be controlled by a controller (not shown).

Due to the substantially inflexible void volume of the conduits and the sorbent cartridge 301, bulk fluid or water is prevented from moving across the membrane 317 from the extracorporeal circuit 330 of the dialyzer 316 to the dialysate circuit 340 of the dialyzer 316. Specifically, due to the controlled compliant feature of the void volume of the dialysis circuit 340, water cannot passively move from the extracorporeal side to the dialysate side through the dialysis membrane. In the event of factors that tend to increase pressure on the extracorporeal side of the dialysis membrane, such as increased blood flow rate or blood viscosity, pressure across the membrane will automatically be equalized due to the limited volume of the dialysis circuit 340 and the non-compressible nature of the dialysate. In the event of factors that tend to increase pressure on the dialysate side of the dialysis membrane 317, such as increased dialysis flow rate, net movement of water from the dialysis circuit 340 to the extracorporeal circuit 330 is prevented by a vacuum that would form in the dialysate circuit 340 in the event of such a movement. Since the dialyzer can be a high flux type, there is some fluid flux back and forth across the dialyzer membrane due to the pressure differential on the blood and dialysate sides of the membrane. This is a localized phenomenon due to the low pressure required to move solution across the membrane and is called backfiltration, however results in no net fluid gain or loss by the patient.

Using the controlled compliance dialysis circuit described herein, net movement of water across the dialysis membrane occurs under active control rather than passively due to pressure differences that develop across the dialysis membrane due to normal operations. A control pump 335 is present and accesses the controlled compliance dialysis circuit 340 through a conduit 336. In certain embodiments, the conduit 336 joins with the controlled compliance dialysis circuit 340 at a point downstream from the dialyzer 316. The control pump 335 can be operated in an influx direction that moves fluid from a control reservoir 337 to the controlled compliance dialysis circuit 340 or in an efflux direction that moves fluid from the controlled compliance dialysis circuit 340 into the control reservoir 337. Due to the substantially inflexible volume of the dialysis circuit 340, volume added to the controlled compliance dialysis circuit when the control pump 335 operates in the influx direction causes net movement of fluid from the dialysate side of the dialysis membrane 317 to the extracorporeal side of the dialysis membrane 317. When the control pump 335 is operated in the efflux direction, fluid is drawn from the extracorporeal side of the dialysis membrane into the controlled compliance dialysis circuit. In certain embodiments, the control pump 335 can be operated at a rate from 0 to about 500 mL/min in either direction.

An infusate pump 304 is used to add a cation infusate 305 into the hemofiltration circuit 340 to generate a fluid having a proper physiological composition to serve as a replacement fluid for introduction into the extracorporeal circuit 330. A bicarbonate solution in a container 306 can further be added by a pump 307 to maintain a physiological pH in the fluid prior to introduction to the extracorporeal circuit.

It will be understood that the connector provides for a fluid connection in its broadest sense and can include any type of tubing, fluid or gas passageway, or conduit between any one or more components of the invention.

The sorbent material within the module can be recharged by passing a solution containing the proper solutes through the layers of the sorbent module. To recharge the sorbent modules in-line, the modules may be connected by wash lines to rechargers, which contain solutions for recharging the modules.

Figure 3:
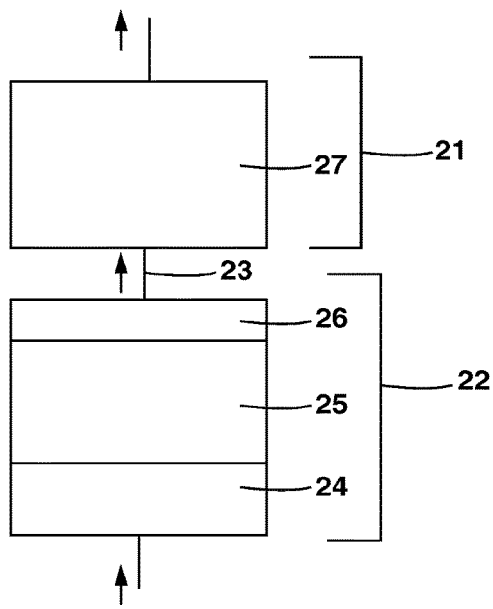
FIG. 3 shows a modular sorbent cartridge with two modules including activated carbon, alumina, urease, and zirconium oxide in the first module and zirconium phosphate in the second module.

One embodiment of the modular sorbent cartridge is shown in FIG. 3. The non-reusable module 22 of the sorbent cartridge can contain layers of activated carbon 24, alumina/urease 25, and hydrous zirconium oxide 26. The reusable module 21 contains zirconium phosphate 27. In certain embodiments, the term non-reusable can refer to the components in a cartridge, and in other embodiments, the term can refer to both the components in the cartridge and the cartridge itself.

After dialysis is complete, the zirconium phosphate layer 27 can contain ammonium, calcium, potassium and magnesium. The module 21 containing the zirconium phosphate may be removed, and the zirconium phosphate can be recharged. The reusable module 21 can be disconnected from the connector 23 connecting the reusable module 21 to the non-reusable module 22, bypass line and/or wash line. The reusable module 21 is then removed from the modular sorbent cartridge. This module 21 can then be recharged, discarded and replaced, or alternatively, the sorbent material within the module can be removed and refilled. It will be understood that any one of the materials used in the present invention can be used multiple times. In such instances of multi-session use, the number of sessions in which one component can be used, can be the same or different from the number of sessions in which another component can be used. In one non-limiting example, a module containing urease may be used two times while another module containing zirconium phosphate can be used three times. In other cases, the module containing urease can be used three times, and the module containing zirconium phosphate used two times. It will be understood that there is no limitation on the numbers of uses for any multi-session use module as compared to another module used in the sorbent cartridge.

Figure 4:
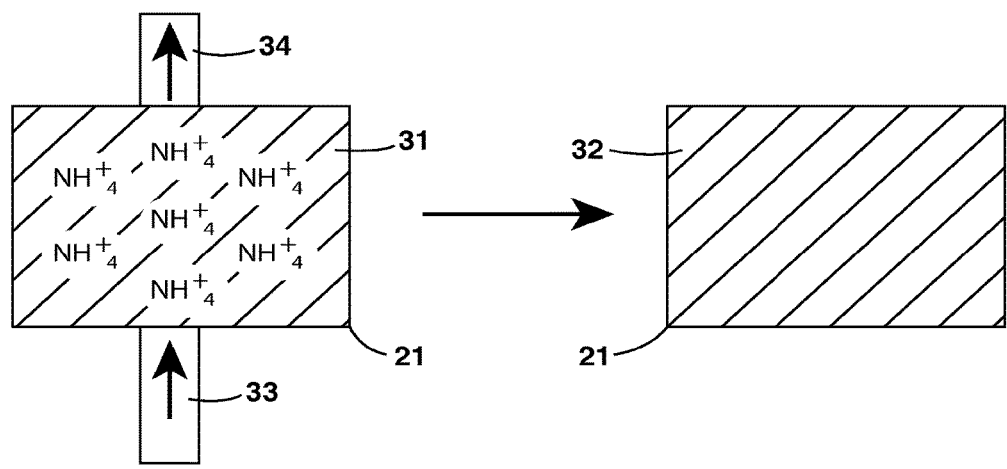
FIG. 4 shows a method for recharging the zirconium phosphate sorbent material.

A method of recharging the zirconium phosphate module is shown in FIG. 4. Wash fluid 33, containing sodium and hydrogen ions, can be passed through the reusable module 21, containing the used zirconium phosphate 31 with bound ammonium ions. This causes an exchange of ions, wherein hydrogen and sodium ions can replace the ammonium ions on the zirconium phosphate 31. The waste fluid exiting the module 34 thus contains the freed ammonium ions with excess sodium and hydrogen ions. This process creates a recharged zirconium phosphate layer 32, containing sodium and hydrogen ions for a subsequent dialysis. In certain embodiments, a recharger can be used to recharge spent sorbent material wherein the recharger contains fluid capable of restoring spent sorbent material to, or near, its original state or usable capacity.

Figure 5:
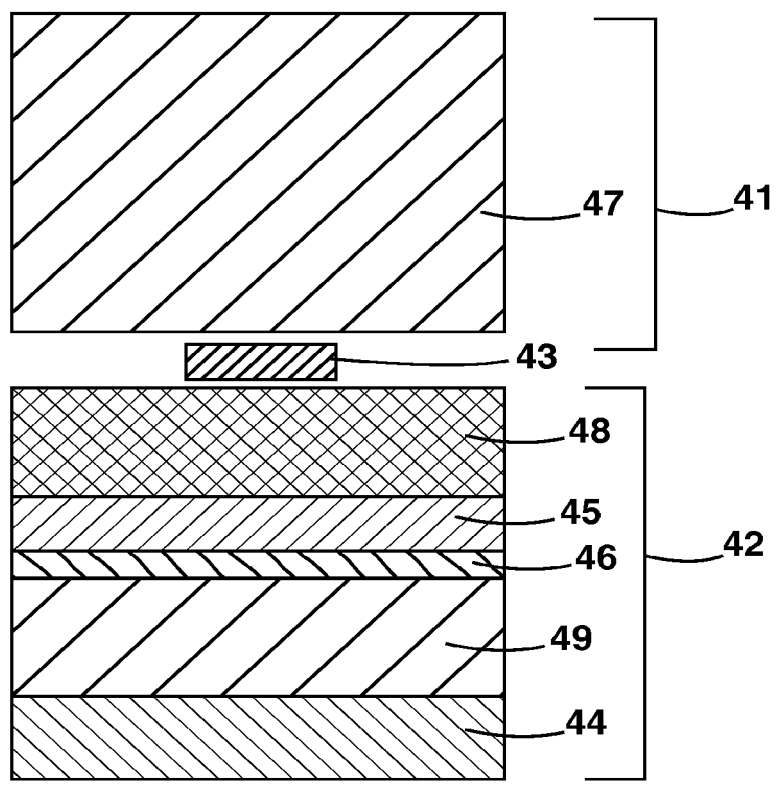
FIG. 5 shows a modular sorbent cartridge with two modules including activated carbon, zirconium phosphate, urease, alumina, and hydrous zirconium oxide in the first module and zirconium phosphate in the second module.

Because calcium and magnesium ions may be more difficult to remove from the zirconium phosphate, and therefore the zirconium phosphate may be more difficult to recharge, it may be advantageous to remove the calcium and magnesium in the first, non-reusable, module so that none of those ions need to be removed in the reusable zirconium phosphate module. Such an embodiment is shown in FIG. 5. Spent dialysate enters the first, non-reusable module 42 where the dialysate can first flow through a layer of activated carbon 44 to remove non-ionic uremic toxins. The dialysate can then enter into a first layer of zirconium phosphate 49. The zirconium phosphate layer 49 can remove the calcium, magnesium and potassium from the fluid. Next the fluid enters the hydrous zirconium oxide layer 46, which removes the phosphate anions and exchanges them with acetate anions. The fluid can then enter the urease layer 45 and alumina layer 48, where the urea is converted to ammonium carbonate and any remaining phosphate ions are removed. In other embodiments of the non-reusable module, any arrangement of the activated carbon, zirconium phosphate, hydrous zirconium oxide layer, and urease and alumina layer is contemplated. For example, the dialysate can first flow through a first layer of zirconium phosphate, activated carbon, then the hydrous zirconium oxide layer, and then enter the urease layer and alumina layer. Alternatively, the dialysate can first flow through the hydrous zirconium oxide layer, then a first layer of zirconium phosphate, the activated carbon, then enter the urease layer and alumina layer. Still further, the dialysate can first flow through the urease layer and alumina layer, then the hydrous zirconium oxide layer, then a first layer of zirconium phosphate, and then the activated carbon. The fluid then flows through the connector 43, and into the second, reusable, sorbent module 41. The sorbent module 41 can contain zirconium phosphate 47. Zirconium phosphate layer 47 can exchange the ammonium ions for sodium and hydrogen. Because the calcium, magnesium and potassium ions have already been removed by the first zirconium phosphate layer 49, the zirconium phosphate layer 47 will not pick up those ions. After dialysis, the second module 41 will only contain zirconium phosphate bound to ammonium ions. As such, the sorbent may be easier to recharge.

In embodiments where one module contains zirconium phosphate and ion-exchange resin, or zirconium phosphate and hydrous zirconium oxide, the module may be recharged in the same manner. The activated carbon layer of a reusable module can be recharged by passing a heated water solution through the module. The alumina/urease layers can be recharged by first passing heated water, or the solutions described above for recharging zirconium phosphate, through the layer, and then passing a solution containing urease through the alumina/urease layer.

Figure 6:
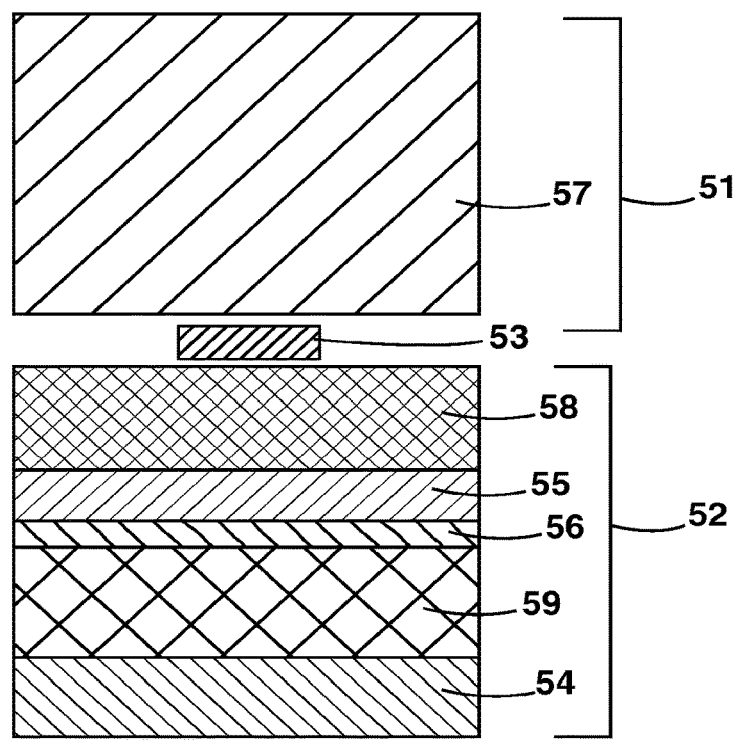
FIG. 6 shows a modular sorbent cartridge with two modules including activated carbon, ion exchange resin, alumina, urease, and hydrous zirconium oxide in the first module and zirconium phosphate in the second module.

Another non-limiting embodiment is illustrated in FIG. 6. Spent dialysate can enter the first, non-reusable, module 52 where it first flows through a layer of activated carbon 54 to remove non-ionic uremic toxins. The spent dialysate then enters into a layer of ion exchange resin 59. The ion exchange resin layer 59 can remove the calcium, magnesium and potassium from the fluid. Next the spent dialysate can enter the hydrous zirconium oxide layer 56, which removes the phosphate anions and exchanges them with acetate anions. The spent dialysate then enters the urease layer 55 and alumina layer 58, where the urea is converted to ammonium carbonate and any remaining phosphate ions are removed. In other embodiments of the first module, any arrangement of the activated carbon, ion exchange resin, hydrous zirconium oxide layer, and urease and alumina layer is contemplated. For example, the dialysate can first flow through an ion exchange resin, activated carbon, then the hydrous zirconium oxide layer, and then enter the urease layer and alumina layer. Alternatively, the dialysate can first flow through the hydrous zirconium oxide layer, then the ion exchange resin, the activated carbon, then enter the urease layer and alumina layer. Still further, the dialysate can first flow through the urease layer and alumina layer, then the hydrous zirconium oxide layer, then the ion exchange resin, and then the activated carbon. The fluid can then flow through the connector 53, and into the second, reusable, sorbent module 51. The sorbent module 51 contains zirconium phosphate 57. The zirconium phosphate layer 57 can exchange the ammonium ions for sodium and hydrogen. Because the calcium, magnesium and potassium ions have already been removed by the ion exchange resin layer 59, the zirconium phosphate layer 57 will not pick up those ions. Alternatively, the ion-exchange resin 59 may be selected to only remove the calcium and magnesium ions, such as by using a chelating ion exchange resin. This can allow use of less of the ion exchange resin. If such a resin is used, the potassium will be removed by the zirconium phosphate 57. Potassium can be easier to remove from zirconium phosphate than calcium or magnesium. In other embodiments, the sorbent materials in each module may be intermixed as opposed to being arranged in layers.

One skilled in the art will recognize that different combinations of sorbent materials in both the reusable and non-reusable modules of the sorbent cartridge can be used without being beyond the scope of this invention. The sorbent materials described herein can be mixed together in any combination as shown in the specific embodiments of the invention.

Figure 7:
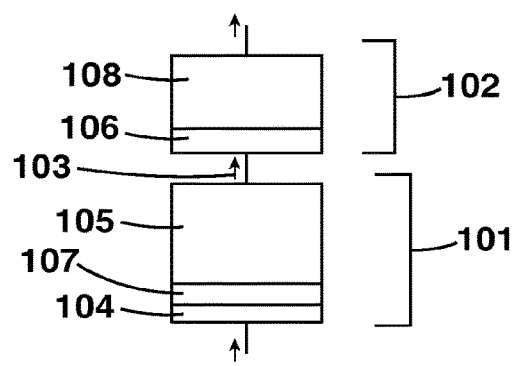
FIG. 7 shows a modular sorbent cartridge with two modules including activated carbon, alumina, urease, and zirconium phosphate in the first module and hydrous zirconium oxide and zirconium phosphate in the second module.

In any embodiment, the sorbent cartridge can be removed from a dialysis system. The sorbent cartridge once removed can be separated into one or more modules to be recharged, disposed of, or recycled. For example, FIG. 7 shows an embodiment wherein the second module contains both hydrous zirconium oxide and zirconium phosphate. The spent dialysate can enter the first module 101. The spent dialysate can first pass through the activated carbon layer 104. The spent dialysate can next pass through a first layer of zirconium phosphate 107, which removes the potassium, calcium and magnesium from the dialysate. Next the spent dialysate can move through the alumina/urease layer 105. In other embodiments of the first module, any arrangement of the activated carbon, zirconium phosphate, and urease and alumina layer is contemplated. For example, the fluid can first flow through activated carbon, then enter the urease layer, and then the zirconium phosphate. Alternatively, fluid can first flow through the zirconium phosphate layer, then activated carbon, and then enter the urease layer and alumina layer. Still further, the fluid can first flow through the urease layer and alumina layer, then the zirconium phosphate, and then the activated carbon. The fluid can then pass through the connector 103, and into the second module 102. The second reusable module 102 contains a hydrous zirconium oxide layer 106, and a second zirconium phosphate layer 108, which removes the ammonium ions from the fluid. After dialysis, the reusable module 102 containing the hydrous zirconium oxide and zirconium phosphate can be recharged, discarded, or the sorbent material removed and new material added. In any embodiment, wash lines may be attached to connector 103 disposed on the reusable module 102 and a second connector positioned after the reusable module 102 wherein the second connector can be positioned thereon or as part of a fluid flow path (not shown).

One skilled in the art will realize that embodiments can be included that involve the sorbent materials being mixed within the module, as opposed to arranging the materials in layers. Such mixing of the sorbent materials can be performed by interspersing the sorbent materials in a single layer by any method known to those of skill in the art.

Figure 8:
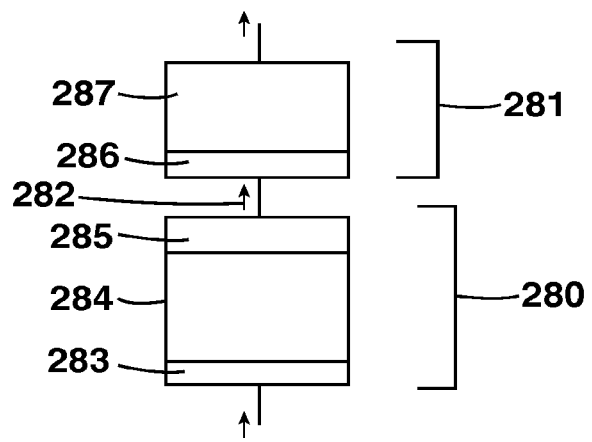
FIG. 8 shows a modular sorbent cartridge with two modules including activated carbon, alumina, urease, and hydrous zirconium oxide in the first module and ion exchange resin and zirconium phosphate in the second module.

Another non-limiting embodiment is shown in FIG. 8. Spent dialysate can enter the first, non-reusable, module 280 where it first flows through a layer of activated carbon 283 to remove non-ionic uremic toxins. The spent dialysate can then enter into a layer of alumina and urease 284, where the urea is converted to ammonium carbonate and phosphate ions are removed. Next the fluid can enter the hydrous zirconium oxide layer 285, which removes the remaining phosphate anions and exchanges them with acetate anions. In other embodiments of the first module, any arrangement of the activated carbon, hydrous zirconium oxide layer, and urease and alumina layer is contemplated. For example, the dialysate can first flow through an activated carbon layer, then through the hydrous zirconium oxide layer, and then enter the urease layer and alumina layer. Alternatively, the dialysate can first flow through a hydrous zirconium oxide layer, then the activated carbon layer and then enter the urease layer and alumina layer. Still further, the dialysate can first flow through the urease and alumina layer, then the activated carbon layer, and then enter the hydrous zirconium oxide layer. The dialysate can first flow through a hydrous zirconium oxide layer, then through the alumina and urease layers, and then flow through the activated carbon layer. Alternatively the dialysate can first flow through the alumina and urease layer, then through the hydrous zirconium oxide layer, and then through the activated carbon layer. The fluid can then flow through the connector 282, and into the second, reusable, sorbent module 281. The sorbent module 281 contains an ion exchange resin layer 286, and a zirconium phosphate layer 287, which removes the ammonium ions from the fluid. In a different embodiment of the second module, the fluid can first pass through the zirconium phosphate layer and then the ion exchange resin. Alternatively, the sorbent materials in each module may be intermixed as opposed to being arranged in layers. After dialysis, the reusable module 281 containing the zirconium phosphate 287 and ion exchange resin 286 can be recharged, discarded, or the sorbent material removed and new material added.

Figure 9:
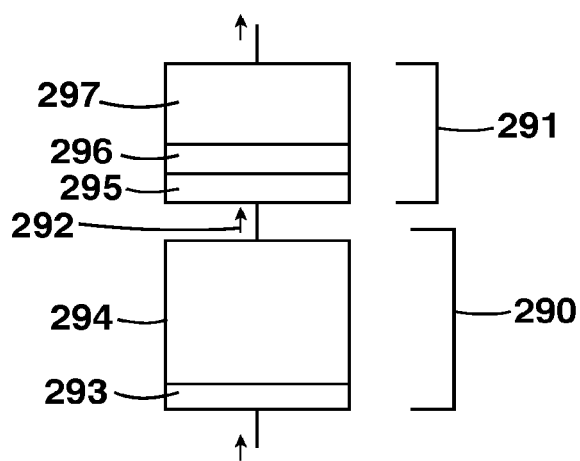
FIG. 9 shows a modular sorbent cartridge with two modules including activated carbon, alumina, and urease in the first module and zirconium oxide, ion exchange resin, and zirconium phosphate in the second module.

As in other embodiments, the hydrous zirconium oxide may be included in the second module as shown in FIG. 9. Spent dialysate can enter the first, non-reusable, module 290 where it first flows through a layer of activated carbon 293 to remove non-ionic uremic toxins. The spent dialysate can then enter into a layer of alumina and urease 294, where the urea is converted to ammonium carbonate and phosphate ions are removed. In another embodiment of the first module, the dialysate can first flow through the alumina and urease, and then flow through the activated carbon. The fluid can then pass through connector 292 and into the second, reusable module 291. The second module 291 contains a layer of hydrous zirconium oxide 295, a layer of ion exchange resin 296 and a layer of zirconium phosphate 297. In other embodiments of the second module, any arrangement of the hydrous zirconium oxide, ion exchange resin and zirconium phosphate is contemplated. For example, the fluid may first pass through a layer of ion exchange resin, then pass through a layer of hydrous zirconium oxide and then pass through the zirconium phosphate. Alternatively, the fluid may first pass through the ion exchange resin, then pass through the zirconium phosphate and then through the hydrous zirconium oxide. Still further, the fluid may pass through the zirconium phosphate, then through the hydrous zirconium oxide, and then through the ion exchange resin. In another embodiment, the fluid can first pass through the hydrous zirconium oxide layer, then through the zirconium phosphate layer, and then through the ion exchange resin. Alternatively, the fluid can first pass through the zirconium phosphate layer, then the ion exchange resin, and then through the hydrous zirconium oxide layer. The sorbent materials in each module can also be intermixed as opposed to being arranged in layers.

Figure 10:
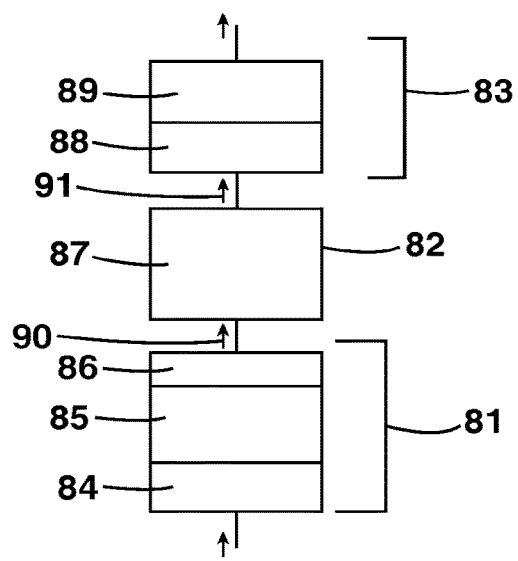
FIG. 10 shows a modular sorbent cartridge with three modules including activated carbon, alumina, urease, and hydrous zirconium oxide in the first module, zirconium phosphate in the second module, and zirconium phosphate and activated carbon in the third module.

The modular sorbent cartridges in this invention are not limited to having two modules. Any number of modules may be utilized in this invention. A three module sorbent cartridge is shown in FIG. 10. The first module 81 contains a layer of activated carbon 84, a layer of alumina/urease 85, and a layer of hydrous zirconium oxide 86. The described layers can also be mixed together rather than being provided in layers. In other embodiments of the first module of a three module sorbent cartridge, any arrangement of the activated carbon, hydrous zirconium oxide layer, and urease and alumina layer is contemplated. For example, the dialysate can first flow through activated carbon, then the hydrous zirconium oxide layer, and then enter the urease layer and alumina layer. Alternatively, the dialysate can first flow through the hydrous zirconium oxide layer, then the activated carbon, then enter the urease layer and alumina layer. Still further, the dialysate can first flow through the urease layer and alumina layer, then the hydrous zirconium oxide layer, and then the activated carbon. The fluid, after passing through these layers, passes through a first connector 90, and into the second module 82. This second module can contain zirconium phosphate 87. The fluid can then pass through a second connector 91, and enter a third module 83. This third module can contain a second layer of zirconium phosphate 88, and a second layer of activated carbon 89 for final purification before passing out of the sorbent cartridge. In other embodiments of the third module of a three module sorbent cartridge, any arrangement of the activated carbon and the second layer of zirconium phosphate are contemplated. For example, the dialysate can first flow through activated carbon and then the second layer of zirconium phosphate. It will be understood that any number of modules can be configured in the present invention. For example, a sorbent cartridge having four, five, six, seven, or more modules is contemplated by the invention. It will be understood that the described arrangements include not just layers, but also the sorbent materials being intermixed.

As each layer of sorbent material within the modular sorbent cartridge may be recharged, a cartridge is possible where all of the modules are reusable. It is still advantageous to utilize separate modules for the sorbent materials in order to direct the correct recharging solution through the correct module, and because different sorbent materials may need to be replaced more often than others.

Because the ability for the zirconium phosphate layer to bind ammonium ions is finite, while the capacity of the urease layer to break down urea into ammonia is not, the capacity of the zirconium phosphate layer may be exceeded. In such a case, excess ammonium ions can be caused to pass through the sorbent cartridge and remain in the dialysate. To protect patient safety, once ammonia breakthrough has occurred, either the dialysis session can be stopped or at least urease can be prevented from catalyzing the conversion of urea to ammonia.

Figure 11:
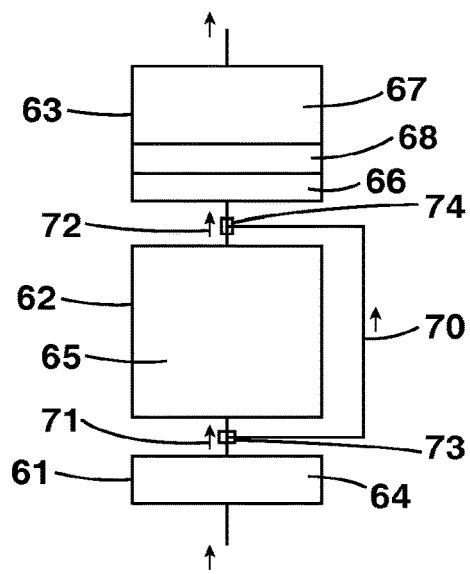
FIG. 11 shows a modular sorbent cartridge with three modules including activated carbon in the first module, alumina and urease in the second module, and ion-exchange resin, zirconium phosphate, and hydrous zirconium oxide in the third module, with an optional bypass line to direct fluid from the first to the third modules.

FIG. 11 shows a three-module sorbent cartridge that can allow bypass of the alumina/urease layer in the case of ammonia breakthrough. Ammonia breakthrough can occur when the capacity of the zirconium phosphate layer to exchange ammonium ions is exceeded. In the event of ammonia breakthrough, the spent dialysate enters the first module 61, which contains the activated carbon layer 64. The spent dialysate then passes through a first connector 71 and by-pass flow valve 73. In normal operation, the flow valve 73 can be set to allow the fluid to pass into the second module 62. The second module can contain alumina/urease layer 65, which catalyzes the breakdown of urea into ammonium ions. The fluid then passes through the second connector 72, by the second valve 74, and into the third module 63. The third module can contain a hydrous zirconium oxide layer 66, ion-exchange resin 68, and zirconium phosphate layer 67. In other embodiments of the third module of a three module sorbent cartridge, any arrangement of the ion-exchange resin, hydrous zirconium oxide layer, and zirconium phosphate layer is contemplated. For example, the dialysate can first flow through ion-exchange resin, then the hydrous zirconium oxide layer, and then enter the zirconium phosphate layer. Alternatively, the dialysate can first flow through the hydrous zirconium oxide layer, then the ion-exchange resin, then enter the zirconium phosphate layer. Still further, the dialysate can first flow through the zirconium phosphate layer, then the hydrous zirconium oxide layer, and then the ion-exchange resin. Again, the described arrangements include not just layers, but also intermixed sorbent materials. After passing through the third module, a regenerated dialysate can exit the sorbent cartridge. In the event of ammonia breakthrough, the first valve 73 can be set to redirect the fluid into bypass line 70. This line will cause the fluid not to enter the second module 62, and therefore the urea will not be broken down into ammonia in the alumina/urease layer 65. The fluid will instead be directed to the second valve 74, where the fluid enters the second connector 72, and then the third module 63. In this way dialysis may continue, while avoiding the creation of ammonia. In certain embodiments either the first valve 73 or the second valve 74 may be optional, and those of skill in the art will recognize that the function can be accomplished with only a single valve if either the first valve 73 or the second valve 74 is a 3-way valve. The valve assembly can also include an access point for a sensor (not shown). The access point can be a portion of the valve assembly wherein a sensor can contact the fluid to take measurement data such as a flow or pressure reading. The form and construction of such access points contemplated by the present invention are those known to one of ordinary skill in the art.

Figure 12:
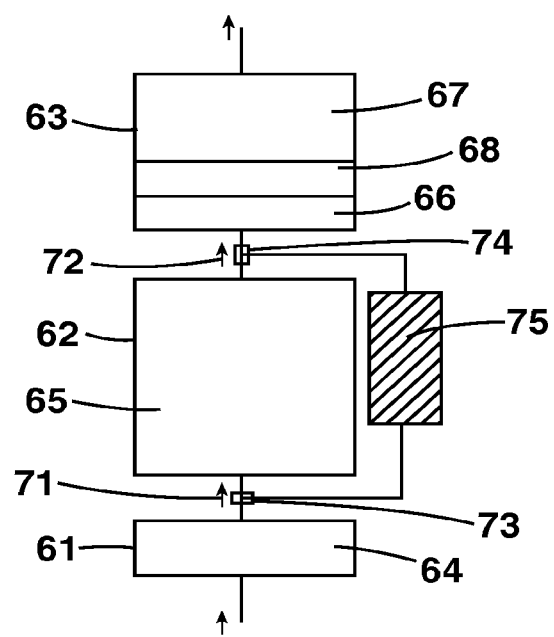
FIG. 12 shows a modular sorbent cartridge with three modules with an optional bypass line connected to another component such as a recharger.

FIG. 12 shows an alternative embodiment to the sorbent cartridge shown in FIG. 11 wherein a first connector 71 and a flow valve 73 bypass flow through the second module 62 to a component 75. The component 75 can be a recharger used to recharge or clean the second module 62 while attached to the sorbent cartridge. In other embodiments, the component 75 can be a container storing a fluid such as a wash fluid or recharging fluid. In still other embodiments, the component 75 can be a pump for pumping fluid. Upon passing through the component 75, fluid can return through the second connector 72 via the second valve 74, and into the third module 63. In some embodiments, the component 75 can be removed after a period of time and fluid allowed to flow to the third module 63 through the second connector 72 and the second valve 74. The component 75 can be reversibly attached and detached as necessary. In certain embodiments either the first valve 73 or the second valve 74 may be optional, and those of skill in the art will recognize that the function can be accomplished with only a single valve if either the first valve 73 or the second valve 74 is a 3-way valve.

To make use of the modular sorbent cartridge easier, the valve assembly may be operated by a programmable controller or computer system that can be programmed to regulate flow through the valves and into and out of the modules. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the modules, in the connectors, or in the valve assemblies. Preferably, the sensors will be placed in a passageway defined between the modules. In certain embodiments, the optical fluid sensors can be connected to an interferometer associated with an opto-electronic demodulator which has an output signal representing the differential pressure between the two sensed areas. In other embodiments, a flow sensing apparatus can have a flow-responsive element projecting into a fluid flow path, and a position sensor associated with the element which detects a change in position of the flow-responsive element in response to the fluid flow. The flow-responsive element can be made of a wide variety of materials having the desired properties known to those of ordinary skill in the art.

It may be advantageous to position multiple modules parallel to each other. This allows fluid to be selectively delivered to one of the parallel modules or to another, or to both simultaneously. Moreover, this allows for one of the parallel modules to go undergo recharging while the dialysis machine, dialysis circuit or dialysis flow path is operational. In particular, the parallel modules can have one module inline and the other module offline.

In certain embodiments, the recharging step can be accomplished with one recharger and three valves. In other embodiments, the recharging step can be accomplished with one or more recharger and any number of valves. It will be understand that additional combinations of valves and rechargers can be implemented to accomplish any desired online/offline state for any combination of modules or sets of modules in parallel. For example, a first set of one or more modules can be in parallel with a second set of one or more modules. As such, the first set of modules can be operated inline and the second set offline. Subsequently, the inline/offline operation can be alternated between the first and second set of parallel modules whereby the first set is offline and the second set is inline. During any offline step, the one or more modules can be recharged. Alternatively, the first and second set of modules can both be simultaneously inline and/or offline. Any number of parallel sets of modules containing any number of modules within each set are contemplated by the invention.

Figure 13:
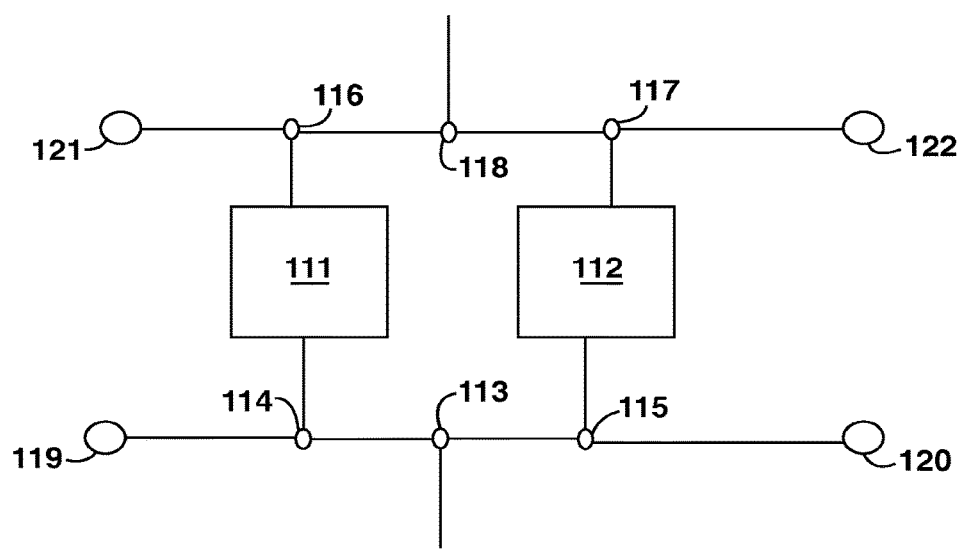
FIG. 13 shows two modules parallel to each other with recharger connectors.

One non-limiting example is shown in FIG. 13. Fluid can pass to a first valve 113. The fluid can then be directed either to a second valve 114 or a third valve 115. The second valve connects to the first module 111. The third valve connects to the second module 112. In this way, fluid may be directed into either the first or the second module. The second valve 114 can also connect to a first recharger connector 119. The third valve 115 can also connect to a second recharger connector 120. Upon exiting the first module 111, fluid will pass to fourth valve 116. Valve 116 can connect to a third recharger connector 121 or a sixth valve 118. Likewise, upon exiting the second module 112, fluid passes to fifth valve 117. Valve 117 can connect to a fourth recharger connector 122, and the sixth valve 118. By selectively directing the flow with the valves, fluid can be caused to pass through either of the two modules parallel to each other. Additionally, fluid may be passed between either module and the rechargers.

Figure 20:
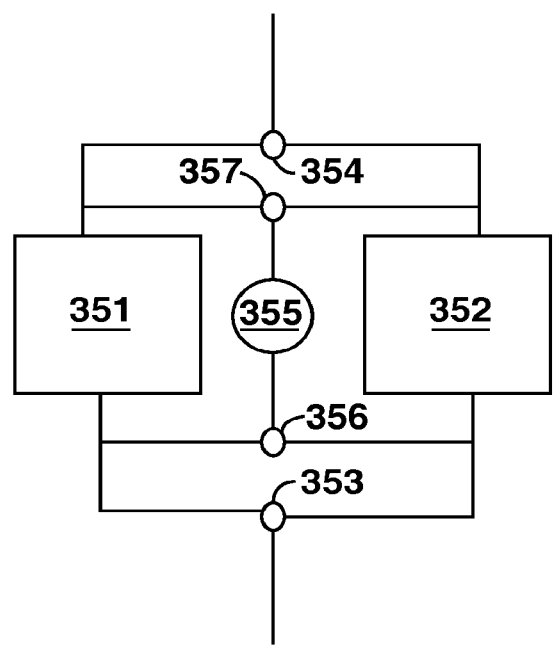
FIG. 20 shows two modules parallel to each other with a single recharger connector.

In an alternative embodiment, shown in FIG. 20, only one recharger is used. Fluid can pass to a first valve 353. Fluid can then be directed either to the first module 351 or the second module 352. Upon exiting either the first module 351 or the second module 352, fluid can pass by the second valve 354. In this way, fluid can be caused to pass through either the first module 351 or the second module 352. Additionally, fluid may be circulated between either module and the recharger 355 by utilizing third valve 356 and fourth valve 357 to direct fluid between either module and the recharger 355. Fluid from the recharger 355 can pass third valve 356, and can then pass into either the first module 351 or the second module 352. Fluid exiting either the first module 351 or second module 352 can be directed by fourth valve 357 back to the recharger 355. Because the modules are parallel, either one may be used or recharged without disrupting the other.

Figure 14:
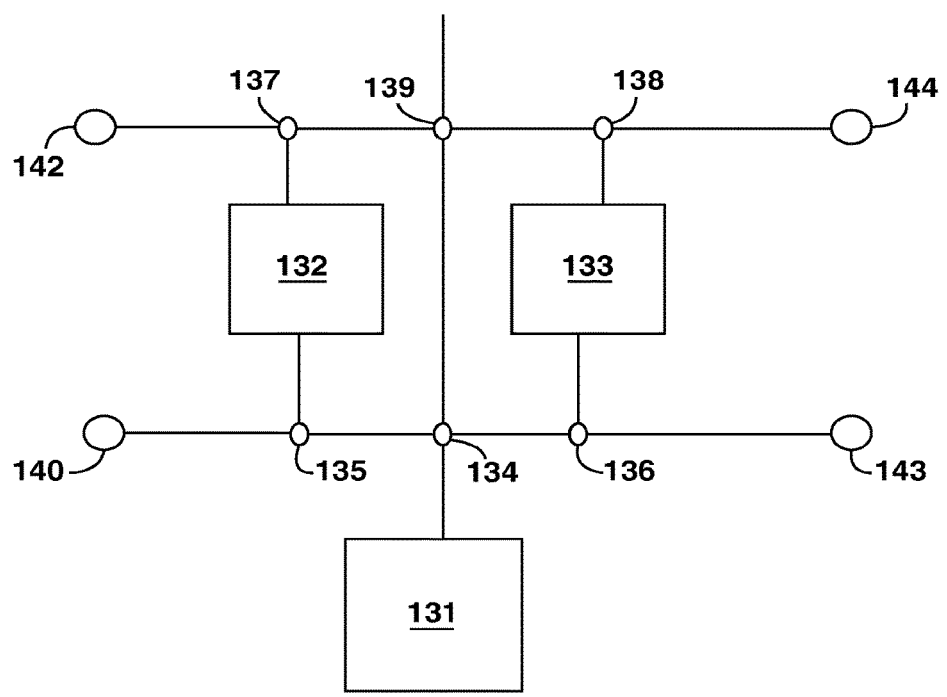
FIG. 14 shows a three module sorbent cartridge where the first module is in series with the second and third modules, wherein the second and third modules are parallel to each other, and includes four recharger connectors.

Because it may be advantageous to put different sorbent materials in different modules for easier recharging of the materials, it would be useful to have the parallel modules in series with one or more other modules. In FIG. 14, the first module 131 is in series with the second and third modules, 132 and 133 respectively, which are parallel to each other. Upon leaving the first module 131, fluid can be directed by the first valve 134 to the second valve 135, third valve 136, or sixth valve 139. If directed to second valve 135, the fluid can then enter the second module 132. If directed to third valve 136, the fluid may then enter the third module 133. If directed toward sixth valve 139, the fluid will bypass both the second and third modules. Additionally, the second valve 135 and third valve 136 can attach to first recharger connector 140 and second recharger connector 143 respectively. Upon exiting the second module 132, fluid passes to fourth valve 137, which is connected to a third recharger connector 142 and sixth valve 139. Upon exiting the third module 133, fluid passes to fifth valve 138, which can connect to a fourth recharger connector 144 and sixth valve 139. By selectively directing the fluid flow path using the valves, fluid may be caused to pass from the first module through either of the second or third modules or to bypass both the second or third module. The second and third modules are both connected to rechargers, wherein fluid can be passed through either recharger selectively without disrupting the other.

Figure 21:
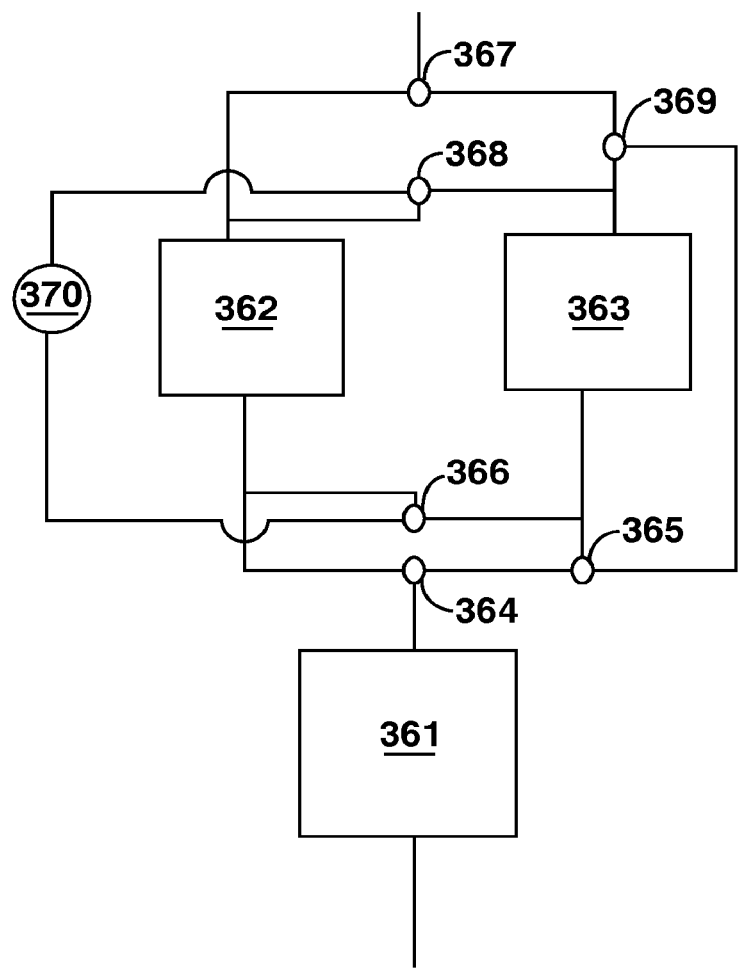
FIG. 21 shows a three module sorbent cartridge where the first module is in series with the second and third modules, and wherein the second and third modules are parallel to each other, and includes one recharger connector.

In an alternative embodiment, a single recharger can be used as shown in FIG. 21. The first module 361 is in series with the second and third modules, 362 and 363 respectively, which are parallel to each other. Fluid leaving the first module 361 can pass valve 364. The fluid can then be directed towards second module 362, or second valve 365. Fluid directed toward the second valve 365 can bypass both the second module 362 and third module 363 through sixth valve 369, or be directed into third module 363. In this way, fluid from the first module 361 may be directed through the second module 362, the third module 363, or neither module. Additionally, fluid may be circulated between either module and the recharger connector 370 by circulating fluid from the recharger connector 370 to third valve 366 and then through either the second or third module. Fluid from the recharger connector 370 can pass third valve 366, and then into either the second module 362 or the third module 363. Because the modules are parallel, either one may be used or recharged without disrupting the other. Fluid exiting the second module 362 or third module 363 can pass through either fourth valve 367 to exit the module, or through fifth valve 368 to circulate with the recharger connector 370.

Figure 15:
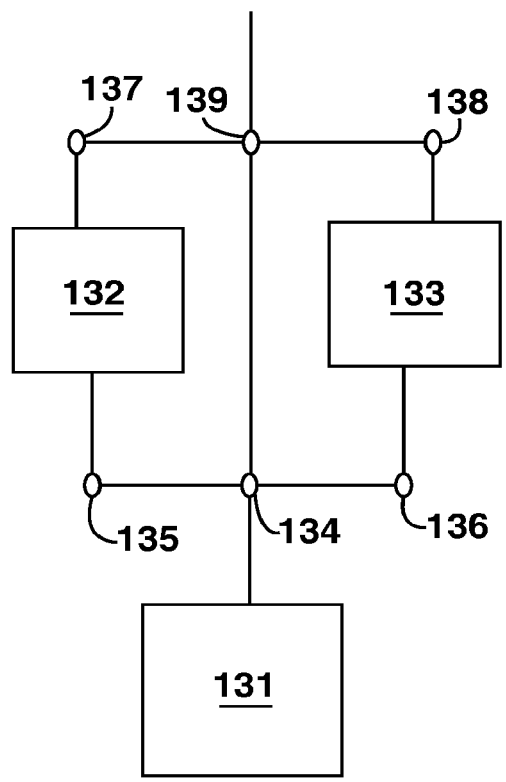
FIG. 15 shows a three module sorbent cartridge where the first module is in series with the second and third modules, wherein the second and third modules are parallel to each other.

In an alternate embodiment, a first module 131 can be placed in series with a second module 132 and third module 133, the latter two of which are parallel to each other, in the absence of a recharger. In FIG. 15, fluid can be directed among and between each of the three modules. This arrangement may be advantageous if different sorbent materials are contained in different modules such that the materials may be recharged without the use of a recharger. Upon leaving the first module 131, fluid can be directed by the first valve 134 to the second valve 135, third valve 136, or sixth valve 139. If directed to second valve 135, the fluid can then enter the second module 132. If directed to third valve 136, the fluid may then enter the third module 133. If directed toward sixth valve 139, the fluid will bypass both the second and third modules.

Figure 16:
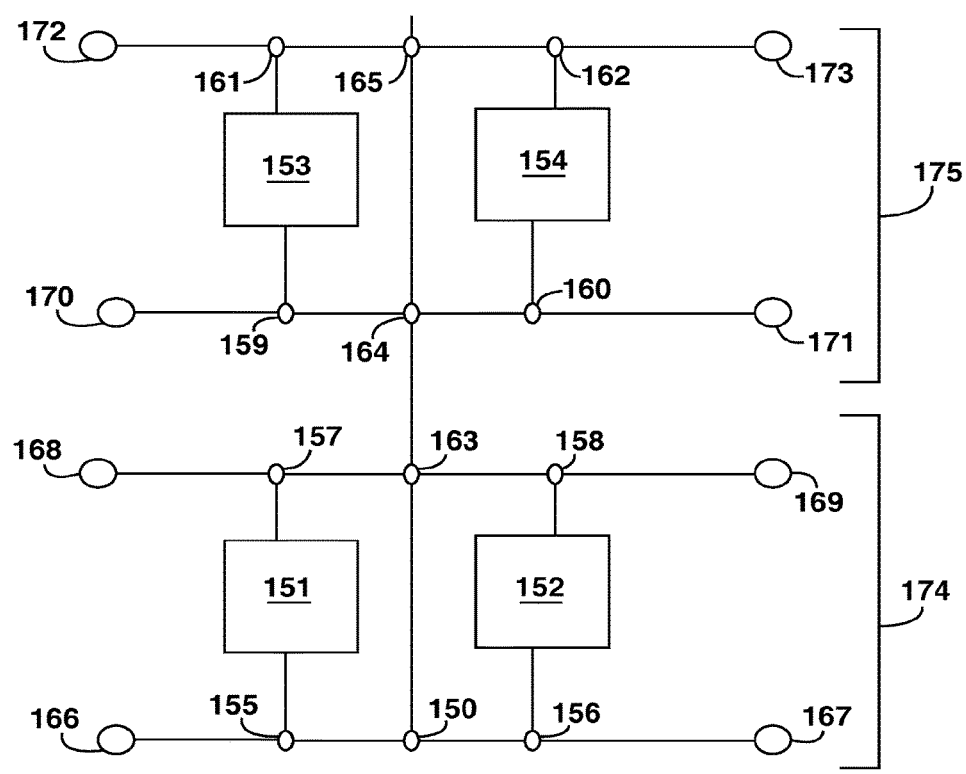
FIG. 16 shows a four module sorbent cartridge with two sets of parallel modules connected to eight recharger connectors and a bypass line.

Another non-limiting embodiment of the invention is contemplated wherein the sorbent cartridge is made up of two sets of parallel modules. Each of these two sets of modules can have two modules that are parallel to one another. In FIG. 16, fluid can pass by a first valve 150 before entering the first set of modules 174. Valve 150 can connect to a second valve 155, third valve 156 and tenth valve 163. The second valve 155 can connect to the first module 151, and also a first recharger connector 166. The third valve 156 can connect to the second module 152, and also a second recharger connector 167. Upon exiting the first module, fluid passes by fourth valve 157, which can connect to a third recharger connector 168, and tenth valve 163. Upon exiting the second module 152, fluid passes to fifth valve 158, which can connect to a fourth recharger connector 169 and tenth valve 163. In this way, fluid can be caused to pass through the first or the second modules of the first set of modules, or to pass through neither of them. Additionally, each module is connected to a recharger, so that each fluid may selectively pass between each module and the proper rechargers.

Similarly, before entering the second set of modules 175, fluid travels from tenth valve 163 to eleventh valve 164. Valve 164 can connect to a sixth valve 159, seventh valve 160 and twelfth valve 165. The sixth valve 159 can connect to a fifth recharger connector 170 and to the third module 153. The seventh valve 160 can connect to a sixth recharger connector 171 and fourth module 154. Upon exiting the third module 153, fluid passes eighth valve 161, which can connect to seventh recharger connector 172 and twelfth valve 165. Upon exiting the fourth module 154, fluid passes ninth valve 162, which can connect to an eighth recharger connector 173 and twelfth valve 165. So fluid may pass through either of the modules in the second set of modules, or it can pass through neither of them. In this way, fluid may selectively travel through either of the modules in the first set of modules, and either of the modules in the second set of modules. Additionally, each module is connected to a recharger so that fluid may selectively pass between the module and the recharger. In certain non-limiting embodiments, if the parallel pairs 153 and 154, and 151 and 152 are not identical (i.e., not four of the same module), two recyclers can be configured one for each pair of parallel modules. In other embodiments, four recyclers can be configured one for each module.

Figure 22:
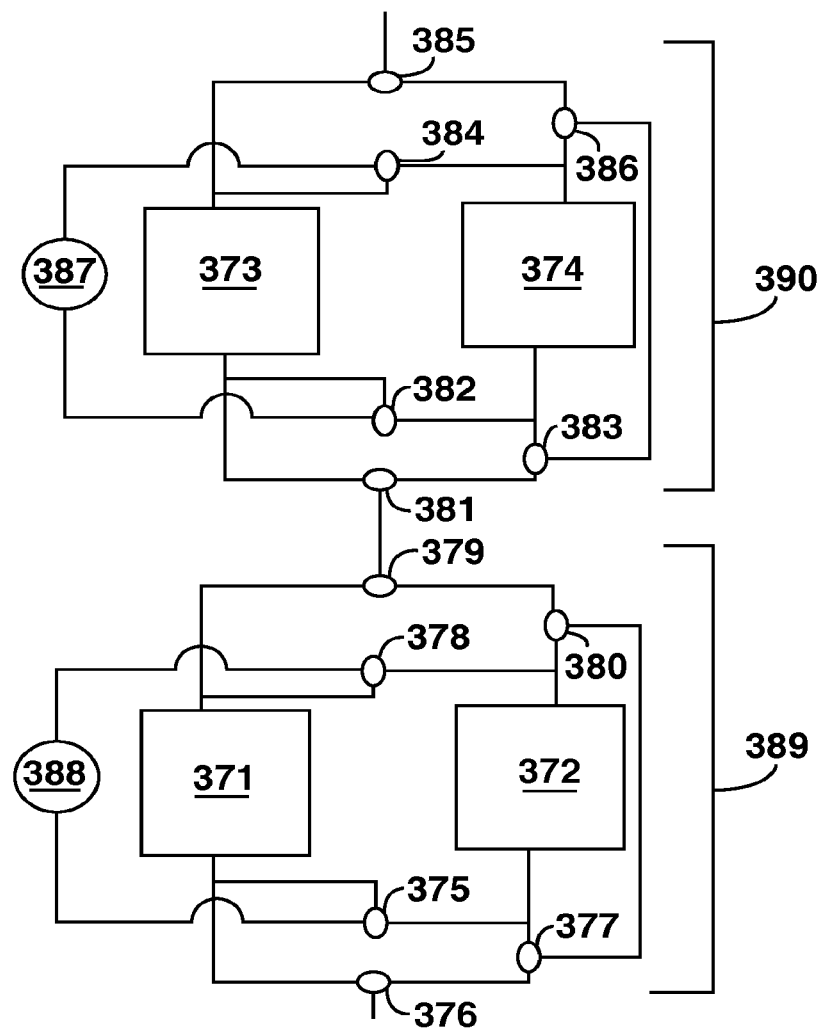
FIG. 22 shows a four module sorbent cartridge with two sets of parallel modules, wherein each set connects to a recharger connector and a bypass line.

An alternative embodiment, utilizing a single recharger connector for each set of parallel modules, is shown in FIG. 22. Fluid can pass by a first valve 376 before entering the first set of modules 389. Valve 376 can connect to a second valve 377, and first module 371. The second valve 377 can connect to the second module 372, or bypass both the first module 371 and second module 372 through sixth valve 380. Additionally, fluid may be circulated between either module and the recharger connector 388 by circulating fluid from the recharger connector 388 to third valve 375 and then through either the first module 371 or second module 372. Fluid from the recharger connector 388 can pass third valve 375 and then into the first module 371 or second module 372. Because the modules are parallel, either one may be recharged or used without disrupting the other. Upon exiting the first module 371 or second module 372, fluid can pass by fourth valve 379, to exit the first set of parallel modules, or fluid can pass by fifth valve 378 to circulate with the first recharger connector 388.

Similarly, before entering the second set of modules 390, fluid travels to seventh valve 381. Seventh valve 381 can connect to a third module 373 and eighth valve 383. The eighth valve 383 can connect to a fourth module 374, or bypass both the third module 373 and fourth module 374 to twelfth valve 386. In this way, fluid from the first set of modules 389 can enter the third module 373, fourth module 374 or bypass both modules. Additionally, fluid may be circulated between either module and the second recharger connector 387 by circulating fluid from second recharger connector 387 to ninth valve 382 and then through either the third module 373 or fourth module 374. Fluid from the recharger connector 387 can pass ninth valve 382, and then into either the third module 373 or the fourth module 374. Because the modules are parallel, either one may be used or recharged without disrupting the other. Fluid exiting the third module 373 or fourth module 374 can pass through either eleventh valve 385 to exit the module, or through tenth valve 384 to circulate with the recharger connector 387.

Figure 17:
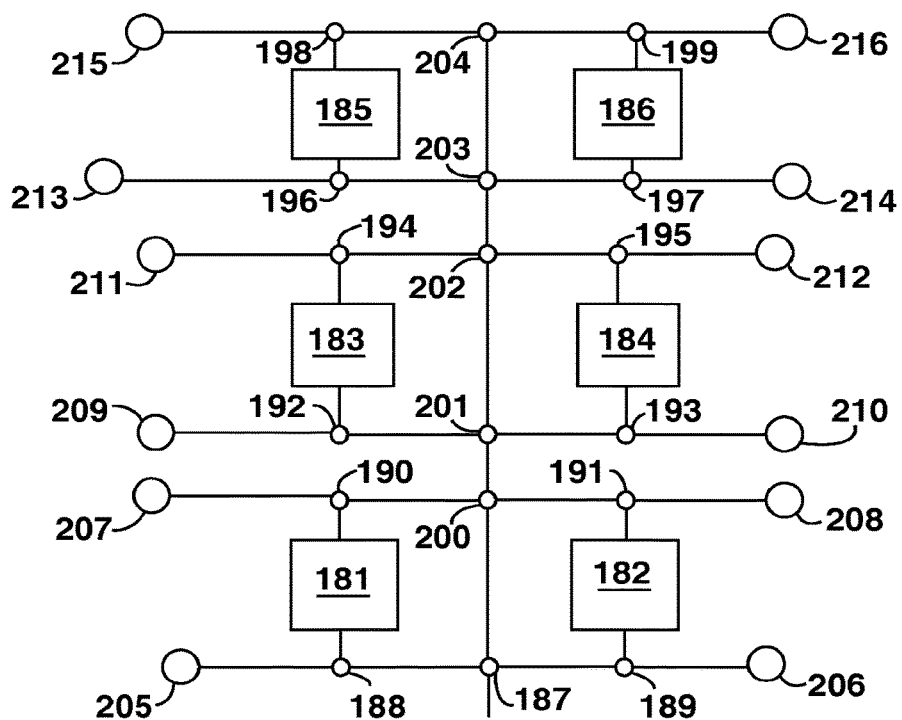
FIG. 17 shows a six module sorbent cartridge with three sets of parallel modules, twelve recharger connectors and a bypass line.

One skilled in the art will recognize that the invention is not limited to systems having two modules, or two sets of parallel modules in series. Multiple modules, or sets of parallel modules, may be set up in series. Additionally, each set of parallel modules may include three or more modules. FIG. 17 shows a sorbent cartridge containing three sets of parallel modules. Fluid passes by a first valve 187 before entering the first set of modules. First valve 187 can connect to a second valve 188, third valve 189 and fourteenth valve 200. The second valve 188 can connect to the first module 181, and also to a first recharger connector 205. The third valve 189 can connect to the second module 182, and also a second recharger connector 206. Upon exiting the first module 181, fluid passes by fourth valve 190, which can connect to a third recharger connector 207, and fourteenth valve 200. Upon exiting the second module 182, fluid passes to fifth valve 191, which can connect to a fourth recharger connector 208 and fourteenth valve 200. In this way, fluid can be caused to pass through the first or the second modules of the first set of modules, or to pass through neither of them by directing flow directly from the first valve 187 to the fourteenth valve 200. Additionally, each module is connected to a recharger, so that each fluid may selectively pass between each module and the proper recharger.

Similarly, before entering the second set of modules fluid travels from fourteenth valve 200 to fifteenth valve 201. Fourteenth valve 200 can connect to a sixth valve 192, seventh valve 193 and sixteenth valve 202. The sixth valve 192 can connect to a fifth recharger connector 209 and to the third module 183. The seventh valve 193 can connect to a sixth recharger connector 210 and fourth module 184. Upon exiting the third module 183, fluid passes eighth valve 194, which can connect to seventh recharger connector 211 and sixteenth valve 202. Upon exiting the fourth module 184, fluid passes ninth valve 195, which can connect to an eighth recharger connector 212 and sixteenth valve 202. So fluid may pass through either of the modules in the second set of modules, or it can pass through neither of them by directing flow directly from the fifteenth valve 201 to the sixteenth valve 202.

The sixteenth valve 202 can connect to seventeenth valve 203. Like the other two sets of modules, before entering the third set, fluid passes by the seventeenth valve 203. Valve 203 can connect to tenth valve 196, eleventh valve 197 and eighteenth valve 204. The tenth valve 196 can connect to the fifth module 185 and a ninth recharger connector 213. The eleventh valve 197 can connect to the sixth module 186 and tenth recharger connector 214. Upon exiting the fifth module 185, fluid passes twelfth valve 198. Twelfth valve 198 can connect the fifth module 185 with the eleventh recharger connector 215 and eighteenth valve 204. Upon exiting the sixth module 186, fluid passes by thirteenth valve 199. Thirteenth valve 199 can connect the sixth module 186 with the twelfth recharger connector 216 and the eighteenth valve 204. So fluid can be made to selectively pass through either of the modules in the third set, or bypass both of them by directing flow directly from the seventeenth valve 203 to the eighteenth valve 204. Additionally, fluid may pass between any of the modules and the rechargers without disrupting the other modules. In certain non-limiting embodiments, if the parallel pairs 181 and 182, and 183 and 184, and 185 and 186, are not identical (i.e., not six of the same module), three recyclers can be configured one for each pair of parallel modules. In other embodiments, six recyclers can be configured one for each module.

Figure 23:
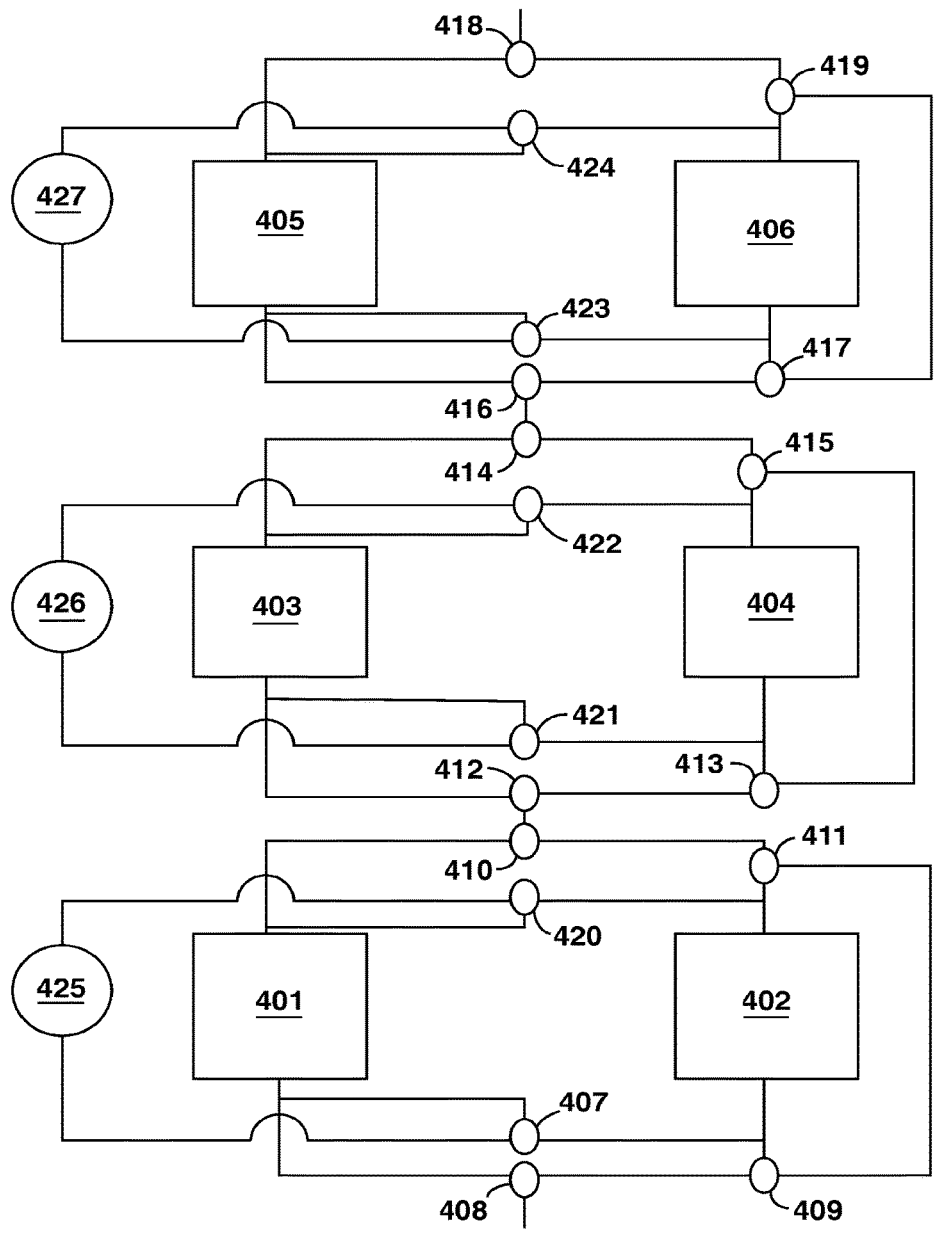
FIG. 23 shows a six module sorbent cartridge with three sets of parallel modules, wherein each set connects to a recharger connector and a bypass line.

An alternative embodiment of the three module system utilizing a single recharger for each set of parallel modules is shown in FIG. 23. Fluid can pass by a first valve 408 before entering the first set of modules. Valve 408 can connect to a second valve 409, and first module 401. The second valve 409 can connect to the second module 402, or bypass both the first module 401 and second module 402 through sixth valve 411. Additionally, fluid may be circulated between either module and the recharger connector 425 by circulating fluid from the recharger connector 425 to third valve 407 and then through either the first module 401 or second module 402. Fluid from the recharger connector 425 can pass third valve 407 and then into the first module 401 or second module 402. Because the modules are parallel, either one may be recharged or used without disrupting the other. Upon exiting the first module 401 or second module 402, fluid can pass by fourth valve 410, to exit the first set of parallel modules, or fluid can pass by fifth valve 420 to circulate with the first recharger connector 425.

Similarly, before entering the second set of modules fluid travels to seventh valve 412. Seventh valve 381 can connect to a third module 403 and eighth valve 413. The eighth valve 413 can connect to a fourth module 404, or bypass both the third module 403 and fourth module 404 to twelfth valve 415. In this way, fluid from the first set of modules can enter the third module 403, fourth module 404 or bypass both modules. Additionally, fluid may be circulated between either module and the second recharger connector 426 by circulating fluid from second recharger connector 426 to ninth valve 421 and then through either the third module 403 or fourth module 404. Fluid from the recharger connector 426 can pass ninth valve 421, and then into either the third module 403 or the fourth module 404. Because the modules are parallel, either one may be used or recharged without disrupting the other. Fluid exiting the third module 403 or fourth module 404 can pass through either eleventh valve 414 to exit the second set of modules, or through tenth valve 422 to circulate with the recharger connector 426.

Before entering the third set of modules fluid travels to thirteenth valve 416. Thirteenth valve 416 can connect to a fifth module 405 and fourteenth valve 417. The fourteenth valve 417 can connect to a sixth module 406, or bypass both the fifth module 405 and sixth module 406 to eighteenth valve 419. In this way, fluid from the first set of modules can enter the fifth module 405, sixth module 406 or bypass both modules. Additionally, fluid may be circulated between either module and the third recharger connector 427 by circulating fluid from third recharger connector 427 to fifteenth valve 423 and then through either the fifth module 405 or sixth module 406. Fluid from the recharger connector 427 can pass fifteenth valve 423, and then into either the fifth module 405 or the sixth module 406. Because the modules are parallel, either one may be used or recharged without disrupting the other. Fluid exiting the fifth module 405 or sixth module 406 can pass through either sixteenth valve 418 to exit the module, or through seventeenth valve 424 to circulate with the recharger connector 427.

Figure 24:
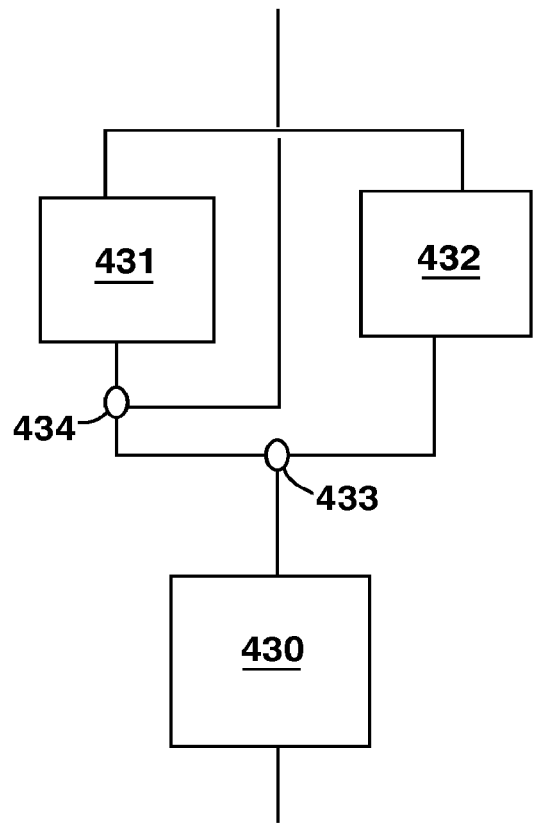
FIG. 24 shows a three module sorbent cartridge where the first module is in series with the second and third modules, and wherein the second and third modules are parallel to each other, with an optional bypass line.

One skilled in the art will understand that the precise number of valves utilized in any embodiment may be altered without being beyond the scope of the invention. Valves may be added or removed to any of the embodiments shown to accomplish the same end. For example, FIG. 24 shows a similar embodiment as is shown in FIG. 15, but uses only two valves. Fluid leaving the first module 430 passes by the first valve 433. First valve 433 can direct fluid either to the third module 432, or to second valve 434. Second valve 434 can direct fluid either into the second module 431, or it can cause the fluid to bypass both modules. In this way, fluid from module 430 may be directed into second module 431, third module 432, or bypass both modules.

Figure 25:
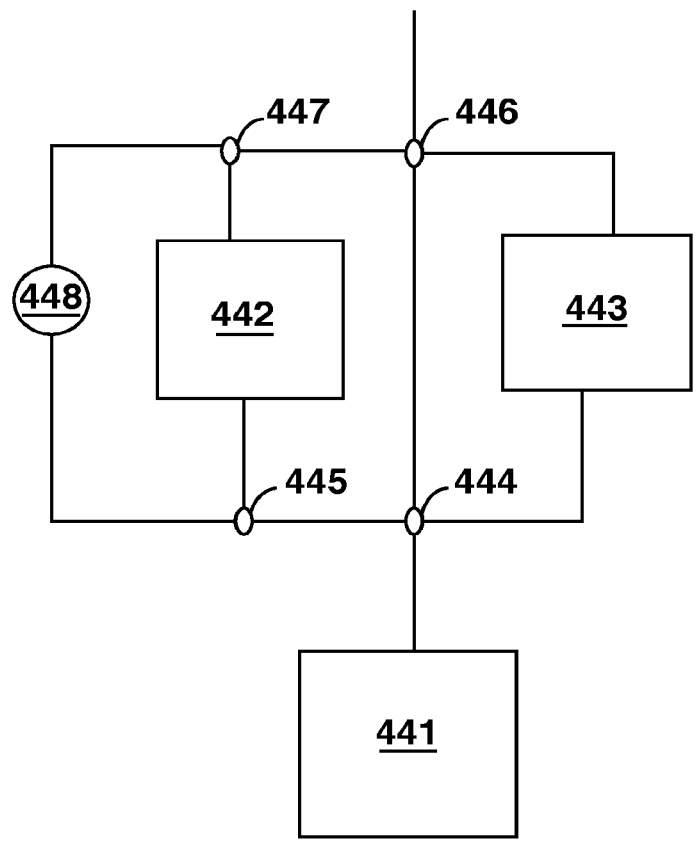
FIG. 25 shows a three module sorbent cartridge where the first module is in series with the second and third modules, and wherein the second and third modules are parallel to each other, with a recharger connector and bypass line.

FIG. 25 shows a similar embodiment as is shown in FIG. 21, but only uses four valves. Fluid leaving the first module 441 passes by first valve 444. First valve 444 can direct fluid either to the third module 443, to second valve 445, or it can cause the fluid to bypass both modules. Second valve 445 can direct fluid either to the recharger connector 448 or into the second module 442. In this way, fluid from the first module 441 can be directed into the second module 442, third module 443, or bypass both modules. Upon exiting the third module 443, or bypassing both the second module 442 and third module 443, fluid passes to fourth valve 446, where it may be directed to another part of the sorbent cartridge. Upon exiting the second module 442, fluid passes to third valve 447, where it may be directed to fourth valve 446 and out of the module. Fluid may be circulated between the second module 442 and the recharger connector 448 by utilizing second valve 445 and third valve 447. Similarly, fluid can be circulated between the recharger connector 448 and the third module 443 by directing fluid by the second valve 445 to the first valve 444, and on into the third module 443.

It will be understood that any number of modules can be configured in the present invention. For example, a sorbent cartridge having four, five, six, seven, or more sets of parallel modules is contemplated by the invention.

In any of the embodiments of this invention, the modules may be made either removable or non-removable. Removable modules may be discarded and replaced, recharged out of line or offline from dialysis, or the sorbent material within the module may be discarded, the module refilled with new sorbent material and then reused. This allows for selective discarding or recycling of one or more modules without removing other modules.

For use in sorbent dialysis, the modular sorbent cartridge should be filled with sorbent material. As spent dialysate moves through the cartridge, the sorbent materials selectively remove specific solutes from the dialysate. Various combinations of sorbent material are known in the art to remove toxins from the spent dialysate. For instance, a sorbent cartridge may be filled with layers of activated carbon, hydrous zirconium oxide, alumina, urease, ion exchange resin and zirconium phosphate. The activated carbon removes non-ionic uremic toxins from the dialysate; the hydrous zirconium oxide removes phosphate and fluoride anions; the alumina/urease catalyzes the breakdown of urea into ammonium ions; and the zirconium phosphate removes the ammonium, calcium, potassium and magnesium ions from the spent dialysate. Each of these layers may be recharged after dialysis to return the layer to its original state or usable capacity.

By placing different sorbent materials in different sorbent modules, the individual modules may be recharged or discarded. One skilled in the art will recognize that the precise order of the layers, and which layers go into which module of a modular sorbent cartridge, may be varied without detracting from the invention. For instance, the first module may be filled with a layer of activated carbon, a layer of hydrous zirconium oxide, and a layer of alumina/urease, while the second module may be filled with zirconium phosphate. Further, the sorbent materials may be mixed in the module, as opposed to arranging the material in layers.

Because, for the purpose of recharging the module, calcium and magnesium may be more difficult to remove from the zirconium phosphate, it may be beneficial to remove these ions prior to the dialysate reaching the zirconium phosphate layer. For instance, a first module may contain layers of activated carbon, ion exchange resin, hydrous zirconium oxide and alumina/urease, while the second module contains zirconium phosphate. The ion exchange resin will remove the calcium, magnesium and potassium so that the only removable cation that remains in the zirconium phosphate layer is ammonium. If a chelating ion exchange resin is employed, the potassium will pass through the ion exchange resin and be removed by the zirconium phosphate. Potassium should be easier to remove from zirconium phosphate during recharging, and this would allow the use of less of the ion exchange resin.

By placing modules in parallel with one another, one of the parallel modules may be recharged by utilizing the attached rechargers utilizing an alternate duty cycle. For instance, if in FIG. 15 the first module 131 contains activated carbon, hydrous zirconium oxide, and alumina/urease and the second module 132 and third module 133 contain zirconium phosphate, then either the second or third module may be selectively recharged in this alternate duty cycle without disrupting the other parallel module.

Similarly, the system in FIG. 16 allows for alternate duty recharging of multiple modules. Either of the sub-modules in each module may be recharging without disrupting the other parallel sub-modules.

In order to ensure that all of the residual fluid is removed from the reusable modules, valves, bypass lines and wash lines, it may be advantageous to blow a gas, such as argon, air, filtered air, nitrogen, helium, or other gas, through the module. The wash line may be adapted so that a gas may be blown through the module instead of, or in addition to, a wash liquid.

Figure 18:
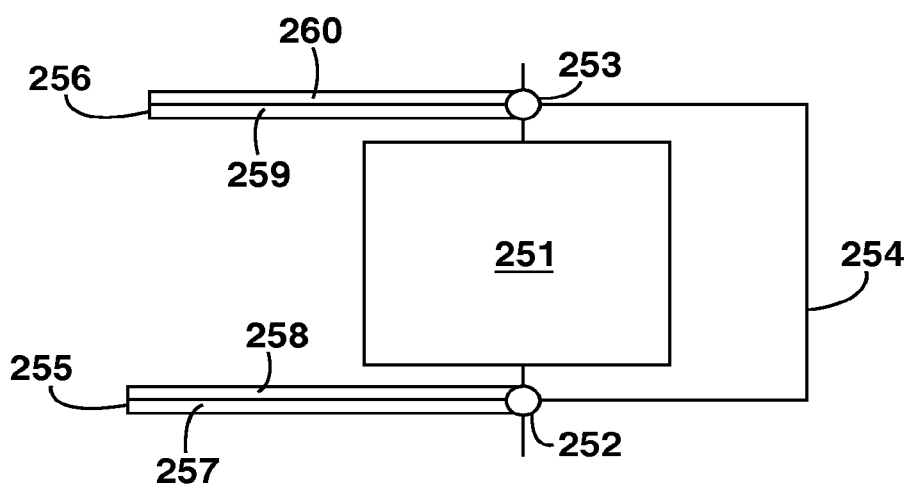
FIG. 18 shows a single module from a modular sorbent cartridge with a bypass line, and two wash lines each divided into gas and fluid wash lines.

Alternatively, a wash line may be divided into two lines as shown in FIG. 18. FIG. 18 shows a first module from an embodiment similar to that shown in FIG. 17 wherein the wash line is adapted to utilize both a liquid and a gas. The first wash line 255 can connect to a first valve 252 positioned before the first module 251. The first valve 252 can also connect to the first bypass line 254. The first bypass line 254 can direct either liquid or gas around the first module 251 to the second valve 253. The first wash line 255 can be further divided into two lines. These lines are the liquid wash line 257, and the gas wash line 258. A second wash line 256 can connect to the second valve 253, and also have both a liquid wash line 259 and a gas wash line 260. This embodiment allows both gas and liquid to pass either into the first module, or to bypass the first module.

Figure 26:
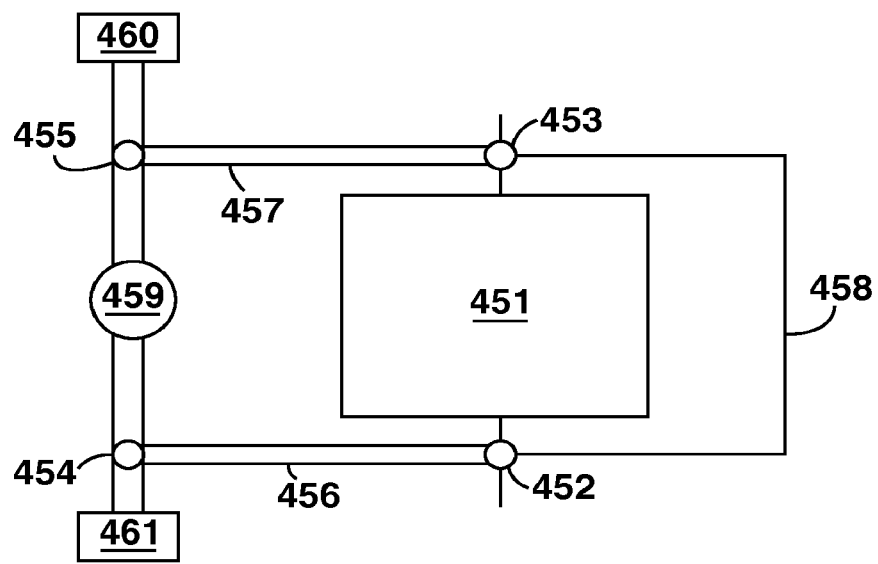
FIG. 26 shows a single module from a modular sorbent cartridge with a bypass line, a recharger connector, and wash lines adapted to move both liquid and gas.

FIG. 26 shows an alternative embodiment utilizing both a gas and liquid line. The first wash line 456 can connect a first valve 454 to a second valve 452. The first valve 454 can be connected to the recharger connector 459, and a fluid collector 461. The recharger connector can also be attached to third valve 455. Third valve 455 can connect the gas source 460 and fourth valve 453 via second wash line 457. Both the second valve 452 and the fourth valve 453 connect to the module 451 and a bypass line 458. This embodiment allows both gas and liquid to circulate through the module 451, or around the module 451.

In addition to dividing the wash line into a gas wash line and a liquid wash line, the wash line may be divided into two different liquid lines. This enables different liquids to travel between the recharger and the modules.

Because the modules in the modular sorbent cartridge may be made detachable, it may be beneficial to include an identification component on the detachable module or modules. This identification component may be a bar code, or any other component that will allow for identification of a particular module. The module then can be matched up to a particular patient, cartridge, or other part of the system to eliminate cross contamination.

It will be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

What is claimed is:

1. A method of recharging a sorbent, comprising the steps of:
    connecting at least a first module and a second module in parallel with one or more connectors;
    fluidly connecting at least one connector to at least one wash line, wherein the at least one wash line is fluidly connected to a recharger;
    fluidly connecting at least one connector to at least one bypass line, wherein the at least one bypass line diverts flow from the connector to bypass at least one module;
    connecting one or more valves to the connectors at junctions between the modules, the at least one bypass line and/or the at least one wash line; and
    selectively opening and closing the valves to direct fluid flow from the recharger through the at least one of the first module and second module to recharge a sorbent in the first module or second module.

2. The method of claim 1, wherein the one or more valves are any one of a two-way, three-way, four-way valve or combinations thereof.

3. The method of claim 1, wherein a valve is positioned on a connector before the first module, the valve connecting the connector, a wash line and the second module, wherein the valve is open to the wash line, and closed to the connector and second module such that flow is directed to a recharger.

4. The method of claim 1, wherein a valve is positioned on a connector before the first module, the valve connecting the connector, a wash line and the second module, wherein the valve is open to the wash line and connector, and closed to the second module such that flow is directed to a recharger.

5. The method of claim 1, wherein a valve is positioned on a connector before the first module, the valve connecting the connector, a wash line and the second module, wherein the valve is open to the second module, and closed to the wash line and the connector, such that flow is directed to the second module.

6. The method of claim 1, wherein a valve is positioned on a connector before the first module, the valve connecting the connector, a wash line and the second module, wherein the valve is open to the connector, and closed to the second module and the wash line, such that flow is directed through the connector and through the first module.

7. The method of claim 1, wherein a pump is attached to the recharger or the at least one wash line.

8. The method of claim 1, further comprising the step of using gas to blow out the module.

9. The method of claim 1, wherein the at least one wash line is subdivided into a top and bottom line.

10. The method of claim 9, wherein the top line is a liquid line and the bottom line is a gas line.

11. The method of claim 9, wherein the top line is a gas line and the bottom line is a liquid line.

12. The method of claim 9, wherein both the top line and the bottom line are liquid lines.

* * * * *